(12) United States Patent
Badal et al.

(10) Patent No.: US 8,357,277 B2
(45) Date of Patent: Jan. 22, 2013

(54) ENHANCED METHOD FOR DETECTING AND/OR QUANTIFYING AN ANALYTE IN A SAMPLE

(75) Inventors: Youssouf Badal, Fremont, CA (US); Ahmed Chenna, Sunnyvale, CA (US); Syed Hasan Tahir, Foster City, CA (US); Yuping Tan, Freemont, CA (US)

(73) Assignee: Laboratory Corp. of America Holdings, Burlington, NC (US)

( * ) Notice: Subject to any disclaimer, the term of this patent is extended or adjusted under 35 U.S.C. 154(b) by 0 days.

(21) Appl. No.: 12/744,749

(22) PCT Filed: Nov. 26, 2008

(86) PCT No.: PCT/US2008/085047
§ 371 (c)(1),
(2), (4) Date: Oct. 18, 2010

(87) PCT Pub. No.: WO2009/070772
PCT Pub. Date: Jun. 4, 2009

(65) Prior Publication Data
US 2011/0180408 A1    Jul. 28, 2011

Related U.S. Application Data
(60) Provisional application No. 60/990,532, filed on Nov. 27, 2007.

(51) Int. Cl.
*G01N 27/447* (2006.01)
(52) U.S. Cl. ..................... 204/452; 204/451
(58) Field of Classification Search ........... 204/450–455
See application file for complete search history.

(56) References Cited

U.S. PATENT DOCUMENTS

| | | | |
|---|---|---|---|
| 2,153,059 A | 4/1939 | Eckert et al. | |
| 2,242,572 A | 5/1941 | Eckert et al. | |
| 3,932,415 A | 1/1976 | Reynolds | |
| 4,105,308 A | 8/1978 | Owen, Jr. et al. | |
| 4,318,846 A | 3/1982 | Khanna et al. | |
| 4,978,632 A * | 12/1990 | Mach et al. ................ | 435/7.36 |
| 4,997,928 A | 3/1991 | Hobbs, Jr. | |
| 5,372,907 A | 12/1994 | Haley et al. | |
| 5,480,968 A | 1/1996 | Kraus et al. | |
| 5,536,834 A | 7/1996 | Singh et al. | |
| 5,677,171 A | 10/1997 | Hudziak et al. | |
| 5,772,997 A | 6/1998 | Hudziak et al. | |
| 5,777,096 A | 7/1998 | Grossman et al. | |
| 5,810,985 A * | 9/1998 | Bao et al. .................. | 204/451 |
| 5,811,098 A | 9/1998 | Plowman et al. | |
| 5,945,526 A | 8/1999 | Lee et al. | |
| 5,958,202 A * | 9/1999 | Regnier et al. ............. | 204/451 |
| 5,968,511 A | 10/1999 | Akita et al. | |
| 6,096,723 A | 8/2000 | Menchen et al. | |
| 6,191,278 B1 | 2/2001 | Lee et al. | |
| 6,322,980 B1 | 11/2001 | Singh | |
| 6,387,628 B1 * | 5/2002 | Little et al. ................. | 506/6 |
| 6,514,700 B1 | 2/2003 | Singh | |
| 6,627,400 B1 | 9/2003 | Singh et al. | |
| 6,630,296 B2 | 10/2003 | Xue et al. | |
| 6,649,351 B2 * | 11/2003 | Matray et al. .............. | 435/6.11 |
| 6,673,550 B2 | 1/2004 | Matray et al. | |
| 6,682,887 B1 | 1/2004 | Singh | |
| 6,686,152 B2 | 2/2004 | Singh et al. | |
| 6,770,439 B2 | 8/2004 | Singh et al. | |
| 6,818,399 B2 | 11/2004 | Singh et al. | |
| 6,846,645 B2 | 1/2005 | Xue et al. | |
| 6,916,612 B2 | 7/2005 | Singh et al. | |
| 6,949,347 B2 | 9/2005 | Singh et al. | |
| 6,955,874 B2 | 10/2005 | Singh et al. | |
| 7,001,725 B2 | 2/2006 | Singh et al. | |
| 7,037,654 B2 | 5/2006 | Chenna et al. | |
| 7,041,459 B2 | 5/2006 | Singh et al. | |
| 7,045,311 B2 | 5/2006 | Ciambrone et al. | |
| 7,105,308 B2 | 9/2006 | Chan-Hui et al. | |
| 7,135,300 B2 | 11/2006 | Chan-Hui et al. | |
| 7,160,735 B2 | 1/2007 | Dehlinger et al. | |

| | | | |
|---|---|---|---|
| 7,217,531 B2 | 5/2007 | Singh et al. | |
| 7,255,999 B2 | 8/2007 | Singh et al. | |
| 7,279,585 B2 | 10/2007 | Singh et al. | |
| 7,312,034 B2 | 12/2007 | Virgos et al. | |
| 7,358,052 B2 | 4/2008 | Singh | |
| 7,402,397 B2 | 7/2008 | Chan-Hui et al. | |
| 7,402,398 B2 | 7/2008 | Pidaparthi et al. | |
| 7,402,399 B2 | 7/2008 | Mukherjeei et al. | |
| 7,537,938 B2 | 5/2009 | Kirakossian et al. | |
| 7,648,828 B2 | 1/2010 | Chan-Hui et al. | |
| 7,771,929 B2 | 8/2010 | Singh et al. | |
| 2002/0045748 A1 | 4/2002 | Drent et al. | |
| 2002/0058263 A1 | 5/2002 | Singh et al. | |
| 2003/0092012 A1 | 5/2003 | Chenna et al. | |
| 2003/0170734 A1 | 9/2003 | Williams et al. | |
| 2003/0175747 A1 | 9/2003 | Singh | |
| 2003/0203408 A1 | 10/2003 | Williams et al. | |
| 2003/0207300 A1 | 11/2003 | Matray et al. | |
| 2003/0235832 A1 | 12/2003 | Chenna et al. | |
| 2004/0029139 A1 | 2/2004 | Singh | |
| 2004/0067498 A1 | 4/2004 | Chenna et al. | |
| 2004/0091850 A1 | 5/2004 | Boone et al. | |
| 2004/0096876 A1* | 5/2004 | Locke et al. | 435/6 |
| 2004/0166529 A1 | 8/2004 | Singh et al. | |
| 2004/0175765 A1 | 9/2004 | Singh et al. | |
| 2004/0197815 A1 | 10/2004 | Singh et al. | |
| 2004/0229293 A1 | 11/2004 | Chan-Hui et al. | |
| 2004/0229294 A1 | 11/2004 | Chan-Hui et al. | |
| 2004/0229299 A1 | 11/2004 | Badal et al. | |
| 2004/0229380 A1 | 11/2004 | Chan-Hui et al. | |
| 2004/0248150 A1 | 12/2004 | Singh et al. | |
| 2004/0265858 A1 | 12/2004 | Singh et al. | |
| 2005/0048553 A1 | 3/2005 | Chenna et al. | |
| 2005/0130238 A1 | 6/2005 | Chan-Hui et al. | |
| 2005/0130246 A1 | 6/2005 | Salimi-Moosavi et al. | |
| 2005/0170438 A1 | 8/2005 | Chan-Hui et al. | |
| 2006/0063269 A1* | 3/2006 | Agnew et al. | 436/86 |
| 2006/0078894 A1* | 4/2006 | Winkler et al. | 435/6 |
| 2006/0199231 A1 | 9/2006 | Moore et al. | |
| 2006/0223107 A1 | 10/2006 | Chenna et al. | |
| 2008/0187948 A1 | 8/2008 | Chan-Hui et al. | |
| 2008/0233602 A1 | 9/2008 | Chan-Hui et al. | |
| 2008/0254497 A1 | 10/2008 | Singh | |
| 2008/0311674 A1 | 12/2008 | Singh et al. | |
| 2009/0011432 A1 | 1/2009 | Chan-Hui et al. | |
| 2009/0011440 A1 | 1/2009 | Mukherjee et al. | |
| 2009/0111127 A1 | 4/2009 | Chan-Hui et al. | |
| 2009/0155818 A1 | 6/2009 | Pidaparthi et al. | |
| 2009/0173631 A1 | 7/2009 | Boone et al. | |
| 2009/0191559 A1 | 7/2009 | Huang et al. | |
| 2010/0143927 A1 | 6/2010 | Sperinde et al. | |
| 2010/0210034 A1 | 8/2010 | Bates et al. | |
| 2010/0233732 A1 | 9/2010 | Bates et al. | |
| 2010/0291594 A1 | 11/2010 | Chan-Hui et al. | |
| 2011/0180408 A1 | 7/2011 | Badal et al. | |

FOREIGN PATENT DOCUMENTS

| | | |
|---|---|---|
| AU | 2001279222 | 8/2001 |
| CA | 2403326 | 11/2001 |
| EP | 1278760 | 6/2008 |
| EP | 1540347 | 9/2009 |
| WO | WO 97/28275 | 8/1997 |
| WO | WO 98/01533 | 1/1998 |
| WO | WO 99/13108 | 3/1999 |
| WO | WO 99/64519 | 12/1999 |
| WO | WO 00/66607 | 11/2000 |
| WO | WO 01/83502 | 11/2001 |
| WO | WO 02/12547 | 2/2002 |
| WO | WO 02/30944 | 4/2002 |
| WO | WO 02/094998 | 11/2002 |
| WO | WO 02/095356 | 11/2002 |
| WO | WO 03/006947 | 1/2003 |
| WO | WO 03/032867 | 4/2003 |
| WO | WO 03/033741 | 4/2003 |
| WO | WO 03/042398 | 5/2003 |
| WO | WO 03/042657 | 5/2003 |
| WO | WO 03/042658 | 5/2003 |
| WO | WO 03/042699 | 5/2003 |
| WO | WO 03/076649 | 9/2003 |
| WO | WO 03/085374 | 10/2003 |
| WO | WO 2004/010842 | 2/2004 |
| WO | WO 2004/011900 | 2/2004 |
| WO | WO 2004/061131 | 7/2004 |
| WO | WO 2004/061446 | 7/2004 |
| WO | WO 2004/063700 | 7/2004 |
| WO | WO 2004/068116 | 8/2004 |
| WO | WO 2004/087887 | 10/2004 |
| WO | WO 2004/091384 | 10/2004 |
| WO | WO 2004/092353 | 10/2004 |
| WO | WO 2005/019470 | 3/2005 |
| WO | WO 2005/037071 | 4/2005 |
| WO | WO 2005/045058 | 5/2005 |
| WO | WO 2005/072507 | 8/2005 |
| WO | WO 2006/044748 | 4/2006 |
| WO | WO 2006/052788 | 5/2006 |
| WO | WO 2006/084018 | 8/2006 |
| WO | WO 2009/070772 | 6/2009 |
| WO | WO 2009/086917 | 7/2009 |
| WO | WO 2010/065568 | 6/2010 |
| WO | WO 2010/083463 | 7/2010 |
| WO | WO 2010/083470 | 7/2010 |

OTHER PUBLICATIONS

Bancroft, J., et al (eds)., Theory and Practice of Histological Techniques, Churchill Livingstone, Edinburgh London and New York, 1977.

Baumstark, A L. The 1,2-dioxetane ring system: Preparation, thermolysis, and insertion reactions. In *Singlet Oxygen*, vol. II (Edited by A. A. Frimer), pp. 1-35. CRC Press, Boca Raton, 1985.

Berger, S. et al. (eds), Guide to Molecular Cloning Techniques, vol. 152, Methods in Enzymology, Academic Press, NY, 1987.

Carey, F. et al. (eds)., Advanced Organic Chemistry : Structure and Mechanisms (Part A & B), 1992.

Corey, E. et al., Intermediaire Dans L'oxydation de Benzylalcoyl Sulfures par L'oxygene Singulet, Tetahedron Letters No. 47, pp. 4263-4266, 1976.

Gennaro, A.R., Remington's Pharmaceutical Sciences, 18th edition.

Creighton, T. Proteins: Structures and Molecular Properties, 2nd edn. W.H. Freeman and Co., New York, 1993.

Haughland, R., Handbook of Molecular Probes and Research Products, Ninth Edition, 2002.

Hermanson, G., Bioconjugate Techniques, 1996, Academic Press, New York.

Innis, M et al. (eds), PCR Protocols: A Guide to Methods and Applications, Academic Press, Inc. 1990.

Kochevar, I. et al., Photosensitized Production of Singlet Oxygen, Methods in Enzymology, vol. 319, pp. 20-28, 2000.

Lehninger, A. et al. (eds), Lehninger Principles of Biochemistry, Worth Publishing, Third Edition, 2000.

Method Booklet 5, Signal Transduction Glossary and Methods, Biosource International, Camarilla, CA, 2000.

Methods in Enzymology, vol. 4, Special Techniques for the Enzymologist, Academic Press, 1965.

Ohlendieck, K., Chapter 28: Extraction of Membrane Proteins, Methods in Molecular Biology, vol. 59, pp. 293-304, 1996.

Pearse, A., Histochemistry: Theoretical and Applied, vol. 1: Preparative and Optical Technology, Fourth Edition, 1980.

Sambrook et al., Molecular Cloning, $2^{nd}$ Edition ed., Cold Springs Harbor Laboratory Press, NY, 1989.

Schlessinger, J., Ligand Induced, Receptor-Mediated Dimerization and Activation of EGF Receptor, Cell, vol. 110, pp. 669-672, 2002.

Skovsen, E. et al., Lifetime and Diffusion of Singlet Oxygen in a Cell, Journal of Physical Chemistry B Letters, vol. 109, pp. 8570-8573, 2005.

Tian, H. et al., Multiplex mRNA Assay using Electrophoretic Tags for High-Throughput Gene Expression Analysis, Nucleic Acids Research, vol. 32, No. 16, e126, 2004.

Ullman, E. et al., Luminescent Oxygen Channeling Immunoassay: Measurement of Particle Binding Kinetics by Chemiluminescence, Prod. Natl. Acad. Sci. USA, vol. 91, pp. 5426-5430, 1994.

Wasserman. H. et al. (eds), Singlet Oxygen, Academic Press, New York, 1979.

Wold, F., Posttranslational Protein Modifications: Perspectives and Prospectives, In: Posttranslational Covalent Modifications of Proteins, pp. 1-12, 1983.

Lee, L. et al., New Energy Transfer Dyes for DNA Sequencing, Nucleic Acids Research, vol. 25, No. 14, pp. 2816-2822, 1997.

Patent Cooperation Treaty, International Search Report and Written Opinion, International Application No. PCT/US08/85047, dated Feb. 12, 2009.

\* cited by examiner

*Primary Examiner* — J. Christopher Ball

(57) ABSTRACT

The invention relates to an enhanced method of detecting and/or quantifying at least one analyte in a sample.

33 Claims, 9 Drawing Sheets

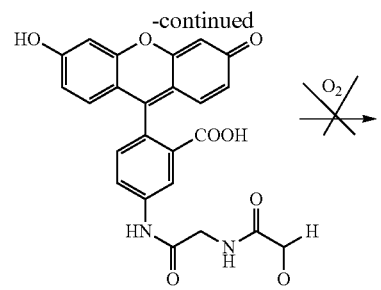

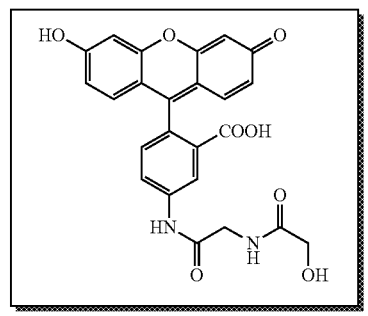

Intermediate Aldehyde

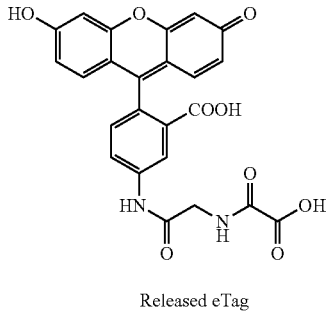

New & only one Product

FIG. 1

4 hrs rx with Pro-11

4 hrs rx with Pro-14

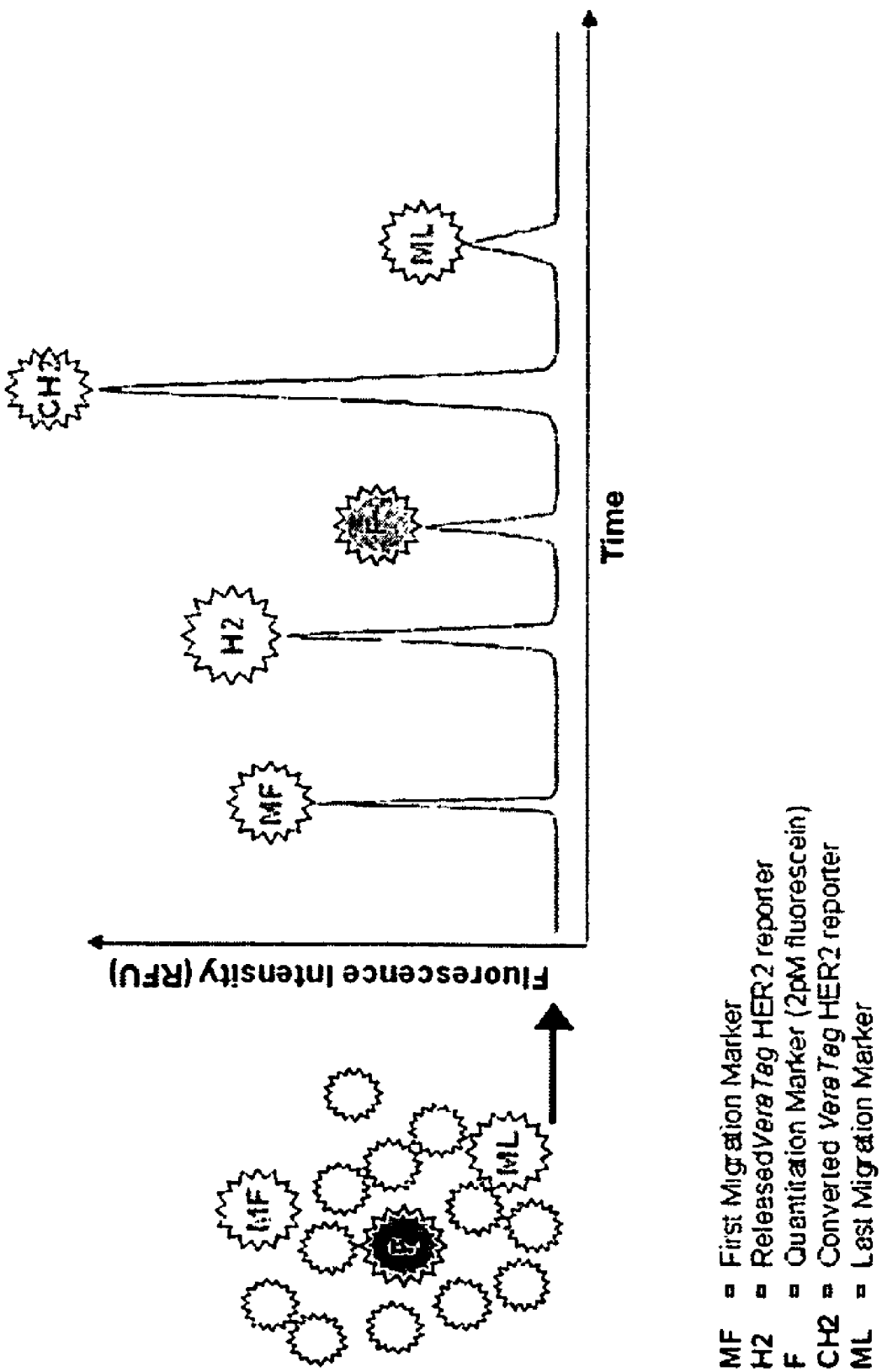

ENHANCED METHOD FOR DETECTING AND/OR QUANTIFYING AN ANALYTE IN A SAMPLE

CROSS-REFERENCE TO RELATED PATENT APPLICATION

This application is a United States national stage parent application of international application No. PCT/US2008/085047, filed Nov. 26, 2008, which claims the benefit of, and claims priority from, U.S. Provisional Patent Application No. 60/990,532, filed Nov. 27, 2007, which is herein incorporated by reference in its entirety.

FIELD OF THE INVENTION

The invention relates to an enhanced method of detecting and/or quantifying at least one analyte in a sample.

BACKGROUND

The need to detect and/or quantify analytes in a sample has become increasingly important. In medicine, for example, there is a need for assays that detect or quantify nucleic acids or polypeptides, as well as a need for assays that detect and quantify proteins interacting with other proteins or proteins interacting with other molecules. There is an especially acute need for such assays in biological samples of interest, such as blood, urine or other biological materials such as tumor samples that have been preserved, or fixed, so that their composition can be readily determined at a time far removed from surgery, for example. Cancer patient would benefit from an assay that could detect and quantify proteins or oligomers or dimers from fixed samples that are harvested at the time of resection and analyzed at much later time.

The current invention provides an enhanced method for detecting and/or quantifying at least one analyte in a sample.

SUMMARY OF THE INVENTION

In one aspect, the invention is drawn to an enhanced method for detecting and/or quantifying at least one analyte in a sample.

In a particular embodiment, the method comprises the steps of:
a. binding a binding compound to an analyte, the binding compound linked to a releasable tag through a linker, the linker containing a singlet oxygen-reactive group;
b. releasing the releasable tag from the binding compound via a singlet oxygen mediated cleavage only if the binding compound has bound to the analyte and generating an intermediate product;
c. reacting the intermediate product with at least one converting agent thereby producing at least one converted product; and
d. detecting the at least one converted product and quantifying the at least one analyte.

In a particular embodiment, the linker is a thioether. In a particular embodiment, the thioether is a compound having the following structure:

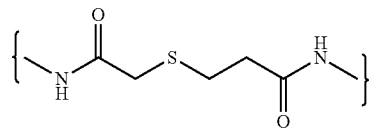

In a particular embodiment, detection and/or quantification of the converted product occurs by electrophoresis. In a particular embodiment, the electrophoresis is capillary electrophoresis. In a particular embodiment, the releasable tag comprises a signal or reporter molecule. In a preferred embodiment, the releasable tag comprises an eTag. In a particular embodiment, the signal or reporter molecule is a fluorescent molecule. In a preferred embodiment, the binding compound comprises an antibody, a protein, an aptamer, a nucleic acid, a peptide nucleic acid or a locked nucleic acid. In a preferred embodiment, the binding compound comprises an antibody. In a preferred embodiment, the releasable tag comprises an eTag and the binding compound comprises an antibody.

The converting agent or the converted product can be any entity useful in carrying out the objects of the invention. In a preferred embodiment, the converting agent comprises a reducing agent, an oxidizing reagent, a Grignard reagent, hydrogen cyanide, an alcohol, an amine, thiol (R—S—H) or bisulfite ($NaHSO_3$). In a preferred embodiment, the converting agent is a reducing agent. Examples of reducing agents or reduction reactions include sodium borohydride ($NaBH_4$), $NaB(CN)_3H$, $H_2$(Ni, Pt, or Pd), Clemmensen reduction Zn(Hg) or Wolff-Kishner reduction. Additional reducing agents are well known to one of skill in the art. In a preferred embodiment, the reducing agent is sodium borohydride ($NaBH_4$). In a preferred embodiment, the converting agent is an oxidizing agent. In a preferred embodiment, the oxidizing agent is $NaOCl/H_2O_2$, $H_2O_2$/air, meta-chloroperoxybenzoic acid (m-CPBA) or OXONE (monopersulfate compound). In a preferred embodiment, the oxidizing agent is m-CPBA. In a preferred embodiment, the converted product is an alcohol, an acid, an acetal, an imine, cyanohydrin, an amine, a thioacetal or a sodium salt of an organic sulfite. In a preferred embodiment, the converted product is an alcohol. In a preferred embodiment, the converted product is an acid.

In a preferred embodiment, the sample is a biological sample. The biological sample can be any sample that may or may not contain an analyte of interest. Biological samples specifically may be almost anything of interest obtained from a patient, such as a human, including but not limited to blood, biological fluids, cells, plasma and most any other tissues. Examples of biological samples include, without limitation, cerebrospinal fluid (hereinafter "CSF"), urine, sputum or fresh tissue. A biological sample may be immediately obtained or may be preserved, or fixed, for analysis at a later time. Methods of fixation can be any that are well-known to one skilled in the art. Such methods of fixation include, but are not limited to, tissue that is Formalin-Fixed, Paraffin-Embedded (hereinafter, "FFPE" tissue), frozen tissue samples or any other fixation method that is known to one skilled in the art. In a preferred embodiment, the sample is an FFPE tissue sample.

In a preferred embodiment, the analyte is a biological molecule of interest. In a preferred embodiment, the analyte is at least one protein. In a preferred embodiment, the analyte is at least one interacting set of proteins, such as, without limitation, at least one oligomer or at least one dimer. In a preferred embodiment, the analyte is at least one nucleic acid, such as, without limitation, a nucleic acid of interest. In a preferred embodiment, the analyte may be used as a biological marker for prediction or prognosis of disease in a patient in need thereof.

In another aspect, the invention is drawn to a method for detecting and quantifying at least one analyte in a sample, the method comprising:

a. binding at least one binding compound to at least one analyte, the binding compound linked to a releasable tag through a linker, the linker containing a singlet oxygen-reactive group;

b. reacting the binding compound with at least one converting agent;

c. releasing the releasable tag from the binding compound only if the binding compound has bound to the analyte, via a singlet oxygen mediated cleavage and producing at least one intermediate product which can be converted to at least one converted product; and d. detecting and quantifying the converted product.

In a particular embodiment, the linker is a thioether. In a particular embodiment, the thioether is a compound having the following structure:

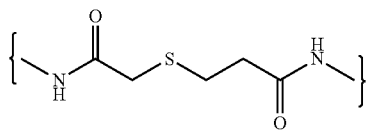

In a particular embodiment, detection and/or quantification of the converted product occurs by electrophoresis. In a particular embodiment, the electrophoresis is capillary electrophoresis. In a particular embodiment, the releasable tag comprises a signal or reporter molecule. In a preferred embodiment, the releasable tag comprises an eTag. In a particular embodiment, the signal or report molecule is a fluorescent molecule. In a preferred embodiment, the binding compound comprises an antibody, a protein, an aptamer, a nucleic acid, a peptide nucleic acid or a locked nucleic acid. In a preferred embodiment, the binding compound comprises an antibody. In a preferred embodiment, the releasable tag comprises an eTag and the binding compound comprises an antibody.

The converting agent or the converted product can be any entity useful in carrying out the objects of the invention. In a preferred embodiment, the converting agent comprises a reducing agent, an oxidizing reagent, a Grignard reagent, hydrogen cyanide, an alcohol, an amine, thiol (R—S—H) or bisulfite (NaHSO$_3$). In a preferred embodiment, the converting agent is a reducing agent. Examples of reducing agents or reduction reactions include sodium borohydride (NaBH$_4$), NaB(CN)$_3$H, H$_2$(Ni, Pt, or Pd), Clemmensen reduction Zn(Hg) or Wolff-Kishner reduction. In a preferred embodiment, the reducing agent is sodium borohydride (NaBH$_4$). In a preferred embodiment, the converting agent is an oxidizing agent. In a preferred embodiment, the oxidizing agent is NaOCl/H$_2$O$_2$, H$_2$O$_2$/air, meta-chloroperoxybenzoic acid (m-CPBA) or OXONE (monopersulfate compound). In a preferred embodiment, the oxidizing agent is m-CPBA. In a preferred embodiment, the converted product is an alcohol, an acid, an acetal, an imine, cyanohydrin, an amine, a thioacetal or a sodium salt of an organic sulfite. In a preferred embodiment, the converted product is an alcohol. In a preferred embodiment, the converted product is an acid.

In a preferred embodiment, the sample is a biological sample. The biological sample can be any sample that may or may not contain an analyte of interest. Biological samples specifically may be almost anything of interest obtained from a patient, such as a human, including but not limited to blood, biological fluids, cells, plasma and most any other tissues. Examples of biological samples include, without limitation, cerebrospinal fluid, CSF, urine, sputum or fresh tissue. A biological sample may be immediately obtained or may be preserved, or fixed, for analysis at a later time. Methods of fixation can be any methods that are well-known to one skilled in the art. Such methods of fixation include, but are not limited to, tissue that is FFPE tissue, frozen tissue samples or any other fixation method that is known to one skilled in the art. In a preferred embodiment, the sample is an FFPE tissue sample.

In a preferred embodiment, the analyte is a biological molecule of interest. In a preferred embodiment, the analyte is at least one protein. In a preferred embodiment, the analyte is at least one interacting set of proteins, such as, without limitation, at least one oligomer or at least one dimer. In a preferred embodiment, the analyte is at least one nucleic acid, such as, without limitation, a nucleic acid of interest. In a preferred embodiment, the analyte may be used as a biological marker for prediction or prognosis of disease in a patient in need thereof.

BRIEF DESCRIPTION OF THE SEVERAL VIEWS OF THE DRAWINGS

These and other features, aspects, and advantages of the present invention will become better understood with regard to the following description, and accompanying drawings, where:

In FIG. 6, Ab-ProX, which contains a linker having a singlet oxygen-reactive group, is illuminated in the presence of a photosensitizer and singlet oxygen is produced. Singlet oxygen cleaves the singlet oxygen-reactive group in the linker and produces an intermediate product. The intermediate product is shown as an aldehyde. The intermediate product is reacted with a converting agent, here an oxidizing agent. A converted product is formed, the so-called "Released eTag."

FIG. 7 illustrates the readable results for particular embodiments of the invention.

FIG. 8 displays the readable results for particular embodiments of the invention showing an electropherogram as set forth in the examples. The converting agent was added after illumination (see FIG. 1 and FIG. 2). The releasable tag is shown here as H2, and the converted product is shown as CH2. MF, F and ML represent internal control peaks, specifically the first migration marker (MF), the last migration marker (ML) and the quantitation marker (F, 3 pM fluorescein). The x-axis shows time in minutes, and the y-axis shows fluorescent intensity as measured in relevant fluorescent units (RFUs).

DETAILED DESCRIPTION OF THE INVENTION

Definitions

Figure 1:
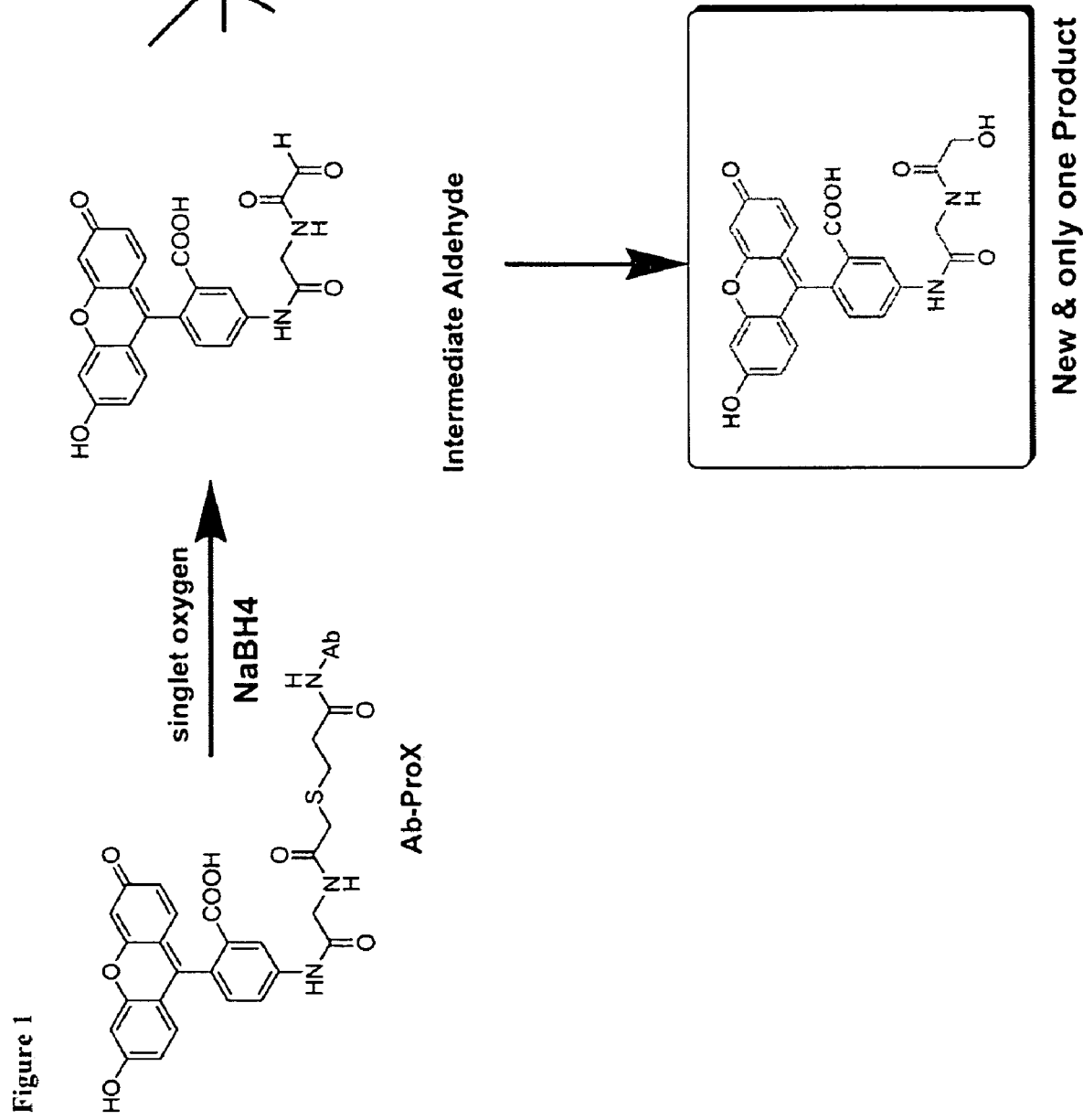
FIG. 1 illustrates a particular embodiment of the invention where addition of a converting agent leads to an enhanced ability to detect and/or quantify an analyte. eTag-X (herein exemplified by Ab-ProX), which contains a linker having a singlet oxygen-reactive group, is reacted with singlet oxygen and NaBH$_4$. Singlet oxygen cleaves the singlet oxygen-reactive group in the linker and produces an intermediate product, which then reacts with NaBH$_4$. A converted product is formed, the so-called "New and only one Product" as set forth in FIG. 1. In the reaction scheme, the "x" indicates a reaction path that is disfavored as a result of addition of the converting agent in the previous step and "Ab" designates an antibody, any antibody, which is in turn attached to the linker. Formation of the converted product leads to an enhanced ability to detect and/or quantify the analyte.
Figure 2:
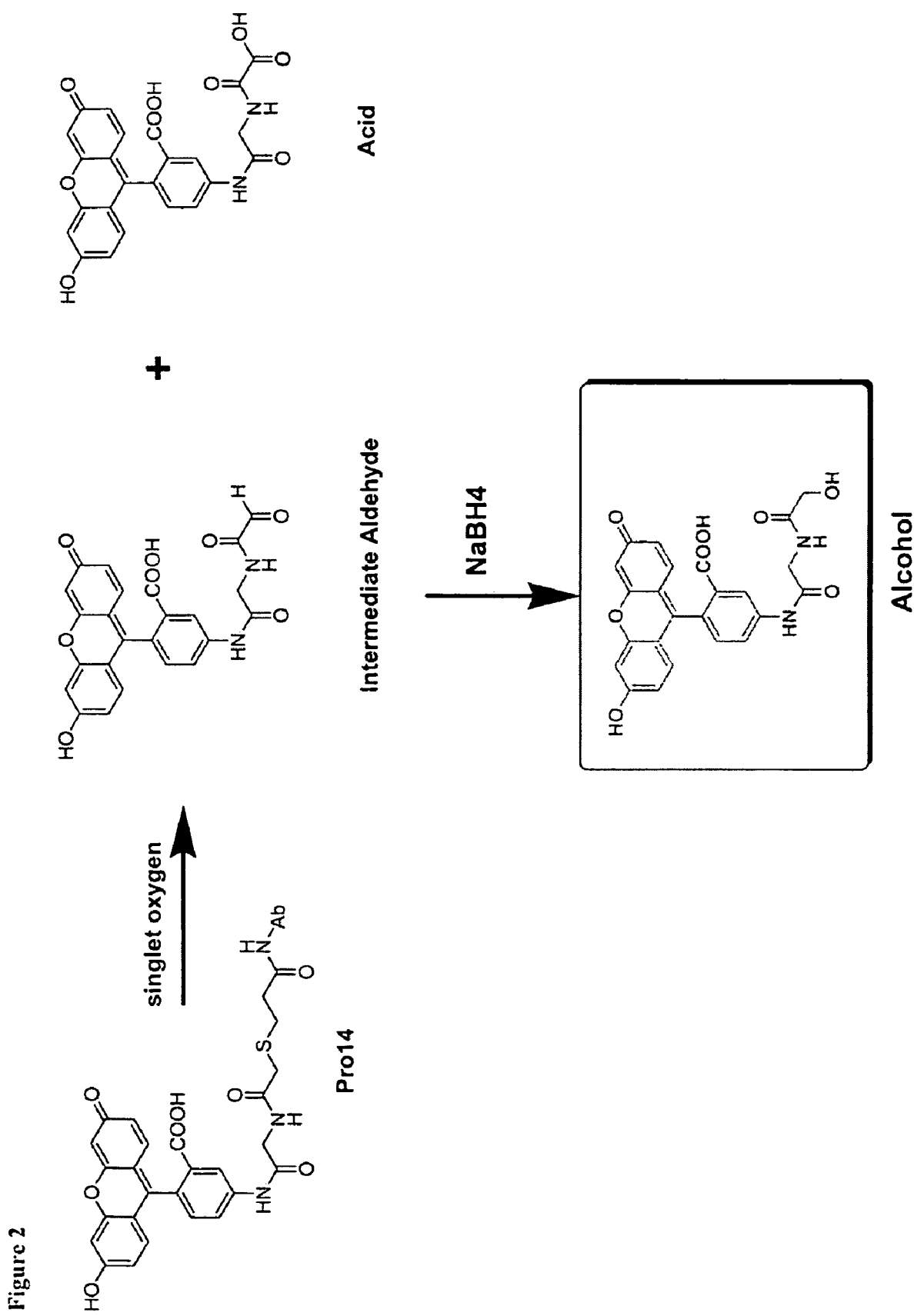
FIG. 2 illustrates a particular embodiment of the invention where addition of a converting agent leads to an enhanced ability to detect and/or quantify an analyte. Ab-Pro-14 (designated Pro 14 in FIG. 2), which contains a linker having a singlet oxygen-reactive group, is illuminated in the presence of a photosensitizer. Singlet oxygen cleaves the singlet oxygen-reactive group in the linker and produces an intermediate product. The intermediate product is shown as an aldehyde. The intermediate product is treated with a converting agent, here a reducing agent, specifically NaBH$_4$, which produces a converted product, in this case an alcohol. A releasable tag is also formed, here an acid. In the reaction scheme, "Ab" designates an antibody, any antibody, which is in turn attached to the linker. Formation of the converted product leads to an enhanced ability to detect and/or quantify the analyte.
Figure 3:
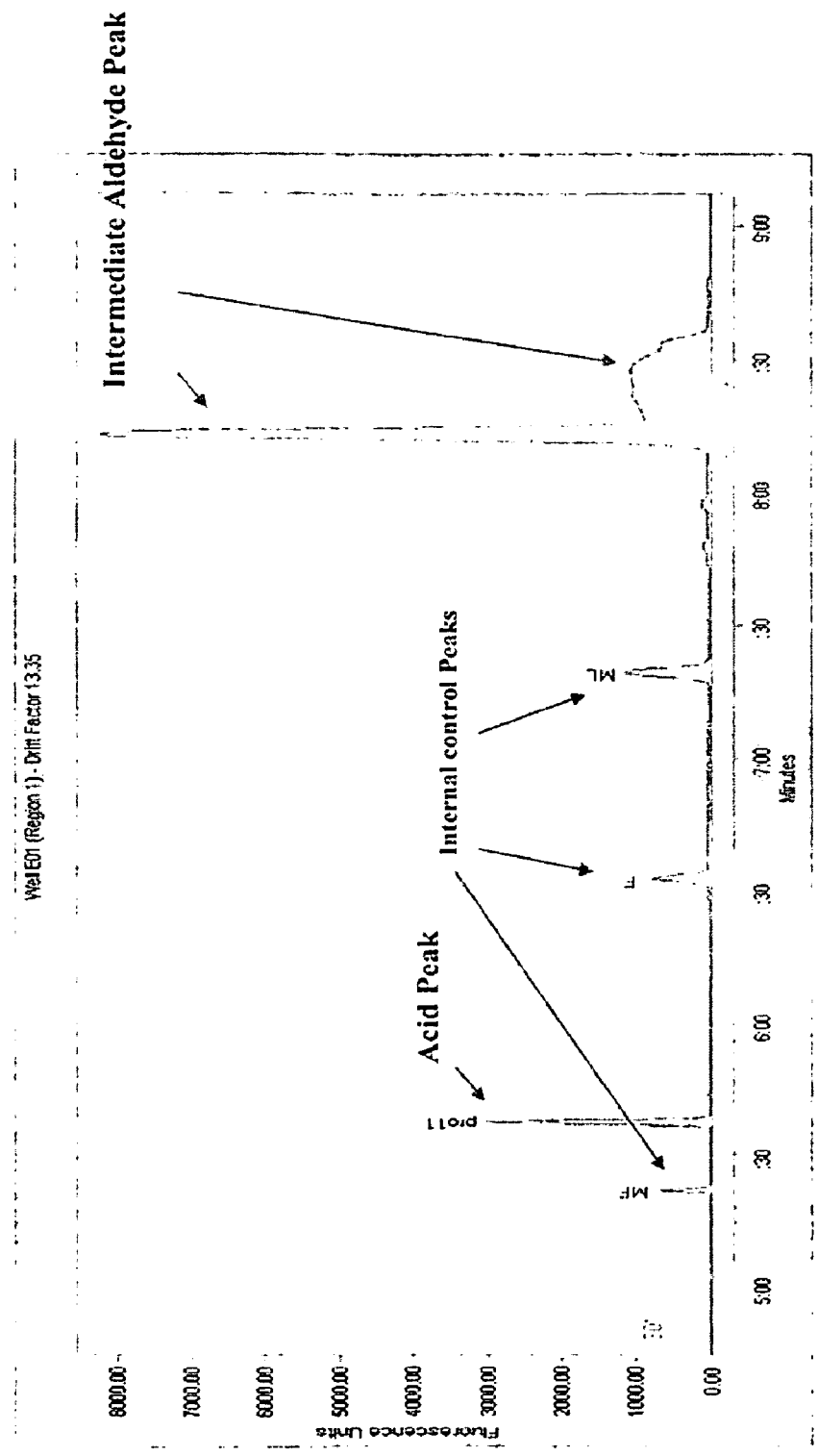
FIG. 3 illustrates the readable results for an electropherogram without addition of a converting agent. The releasable tag is an acid, here shown as Pro11. An intermediate product, here shown as the "Intermediate Aldehyde Peak," can be seen on the right hand side of the electropherogram. The x-axis shows time, in minutes, and the y-axis shows fluorescence units as described in Example 2 and throughout the specification. MF, F and ML represent internal control peaks, specifically the first migration marker (MF), the last migration marker (ML) and the quantitation marker (F, 3 pM fluorescein).
Figure 4:
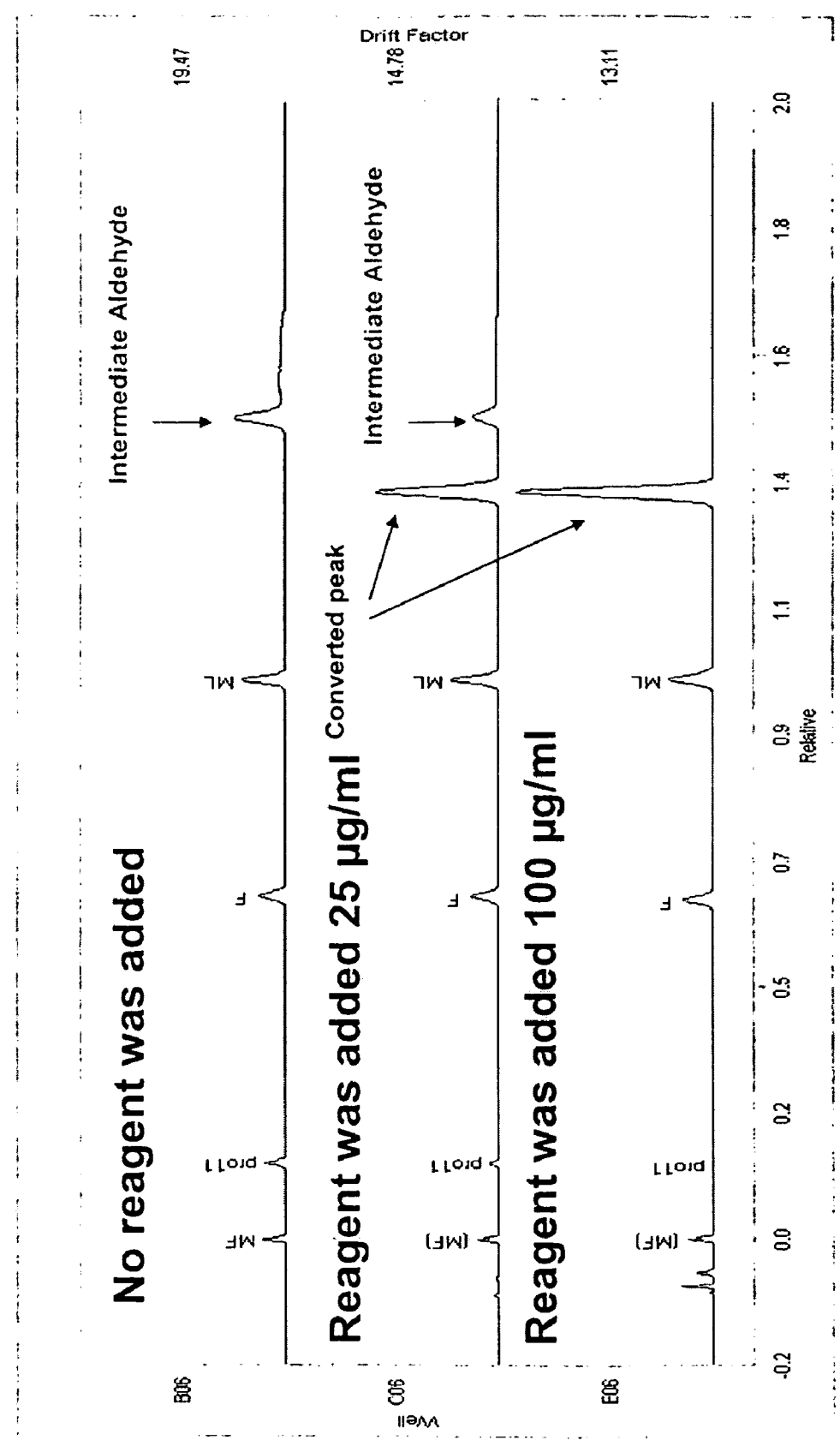
FIG. 4 illustrates the readable results for a particular embodiment of the invention in the form of three electropherograms, one showing the lack of a converting agent (top) and the other two showing the addition of a converting agent (bottom two). The converting agent is a reducing agent, $NaBH_4$, which was added before illumination (see FIG. 1). The releasable tag is an acid, here shown here as Pro11. "Intermediate Aldehyde Peak" designates the intermediate product and can be seen on the right hand side of the top electropherogram. The x-axis shows relative movement, and the y-axis shows the height of the peak as described in Example 2 and as described herein. MF, F and ML represent internal control peaks, specifically the first migration marker (MF), the last migration marker (ML) and the quantitation marker (F, 3 pM fluorescein), and here the term "reagent" is used synonymously with converting agent. Formation of the converted product peak leads to an enhanced ability to detect and/or quantify the analyte (bottom).
Figure 5:
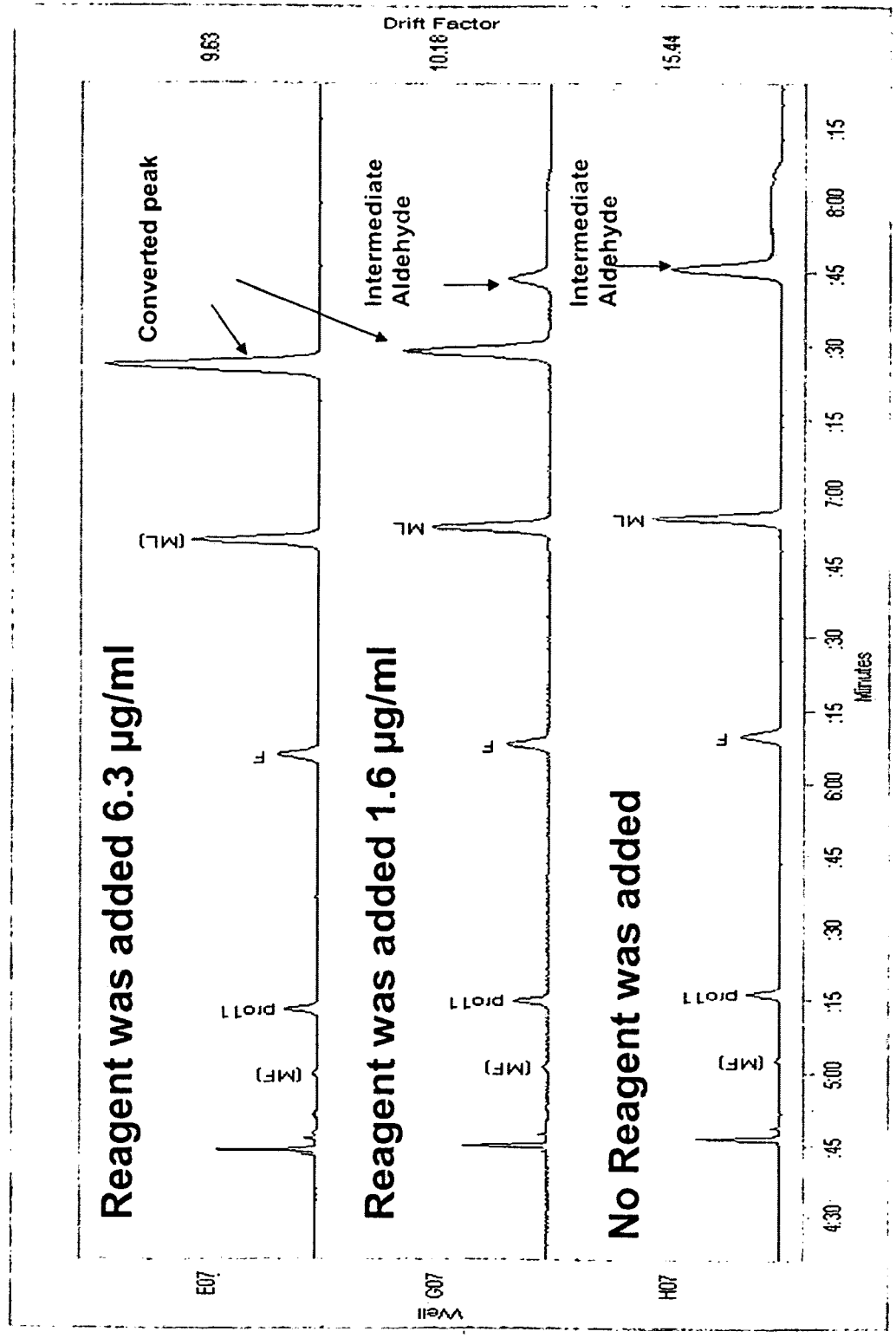
FIG. 5 illustrates the readable results for a particular embodiment of the invention in the form of three electropherograms with converting agents added at concentrations of 6.3 ug/ml (top), 1.6 ug/ml (middle) and 0 (bottom). The converting agent is a reducing agent, $NaBH_4$, and was added after illumination (also see FIG. 1 and FIG. 2). The releasable tag is an acid, here shown here as Pro11. "Intermediate Aldehyde Peak" designates the intermediate product and can be seen on the right hand side of the middle and bottom electropherograms. The x-axis shows movement in minutes, and the y-axis displays the relative height of the peak as described example 2. MF, F and ML represent internal control peaks specifically the first migration marker (MF), the last migration marker (ML) and the quantitation marker (F, 3 pM fluorescein). Formation of the converted product peak leads to an enhanced ability to detect and/or quantify the analyte (top).
Figure 6:
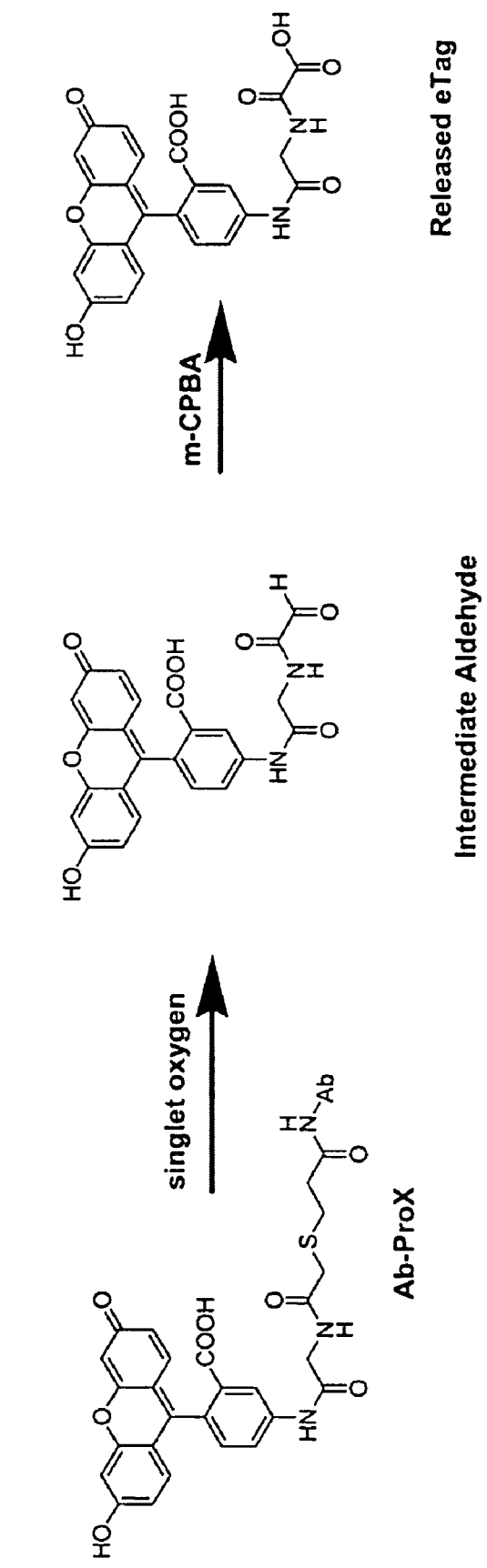
FIG. 6 illustrates particular embodiments of the invention where addition of a converting agent leads to an enhanced ability to detect and/or quantify an analyte.

Terms used in the claims and specification are defined as set forth below unless otherwise specified.

"Analyte" refers to a substance that can be detected or quantified by an analytical procedure, such as the analytical procedure set forth in the invention. An analyte may be, for example, any chemical or biological substance. Non-limiting examples of analytes include, for example, hormones, peptides, proteins, nucleic acids, micromolecules, macromolecules, tissues or mixtures thereof. Analyte may also comprise, for purposes of this invention, detection and/or quantification of interacting proteins, such as dimers and oligomers. Dimer in reference to analytes refers to a stable, usually non-covalent, association of two associated analytes. A dimer of membrane-associated analytes may form as the result of interaction with a ligand, i.e. ligand-induced dimerization (see, e.g. Schlessinger, Cell, 110: 669 672 (2002)). Oligomer in reference to analytes refers to a stable, usually non-covalent, association of at least two associated analytes.

"Antibody" refers to an immunoglobulin that specifically binds to, and is thereby defined as complementary with, a particular spatial and polar organization of another molecule. The antibody can be monoclonal or polyclonal and can be prepared by techniques that are well known in the art such as immunization of a host and collection of sera (polyclonal) or by preparing continuous hybrid cell lines and collecting the secreted protein (monoclonal) or by cloning and expressing nucleotide sequences or mutagenized versions thereof coding at least for the amino acid sequences required for specific binding of natural antibodies. Antibodies may include a complete immunoglobulin or fragment thereof, which immunoglobulins include the various classes and isotypes, such as IgA, IgD, IgE, IgG, IgG2a, IgG2b and IgG3, IgM, etc. Fragments thereof may include Fab, Fv and F(ab')2, Fab' and the like. In addition, aggregates, polymers and conjugates of immunoglobulins or their fragments can be used where appropriate so long as binding affinity for a particular polypeptide is maintained.

"Binding compound" refers to any molecule to which molecular tags can be directly or indirectly attached that is capable of specifically binding to a membrane-associated analyte. Binding moieties include, but are not limited to, antibodies, antibody binding compositions, peptides, proteins, particularly secreted proteins and orphan secreted proteins, nucleic acids and organic molecules, consisting of atoms selected from the group consisting of hydrogen, carbon, oxygen, nitrogen, sulfur and phosphorus.

"Converted product" refers to a compound that is produced by reacting an intermediate product with a converting agent.

The converted product can be detected and/or quantified with a process such as by electrophoresis. The converted product can be, e.g., an alcohol, an acid, an acetal, an imine, a cyanohydrin, a thioacetal, sodium salt of an organic sulfite or an amine. In a preferred embodiment, the converting agent comprises a reducing agent. In a preferred embodiment, the reducing agent comprises sodium borohydride (NaBH$_4$). In a preferred embodiment, the intermediate product is an aldehyde and the converted product is a product that can be measured, e.g., by electrophoresis. A converting agent can be a reducing agent, an oxidizing reagent, a Grignard reagent, hydrogen cyanide, an alcohol, a thiol, a bisulfite or an amine. In a preferred embodiment, the converting agent is an oxidizing agent.

"Converting agent" refers to an agent that is used to convert an intermediate product to a converted product by reacting the intermediate product with the converting agent. In a preferred embodiment, the converting agent comprises a reducing agent. In a preferred embodiment, the reducing agent comprises sodium borohydride (NaBH$_4$). In a preferred embodiment, the intermediate product is an aldehyde and the converted product is a product that can be measured, e.g., by electrophoresis. The converted product can be, e.g., an alcohol, an acid, an acetal, an imine, a cyanohydrin, a thioacetal, sodium salt of an organic sulfite or an amine. A converting agent can be a reducing agent, an oxidizing reagent, a Grignard reagent, hydrogen cyanide, an alcohol, a thiol, a bisulfite or an amine. In a preferred embodiment, the converting agent is an oxidizing agent.

"Electrophoretic tag" refers to a composition or reagent for unique identification of an entity of interest during separation. The concept of an electrophoretic tag is consistently referred to herein as an "e-tag", or "VeraTag," however various references to "Etag", "ETAG", "eTAG" and "eTag" may be made when referring to an electrophoretic tag. E-tags of the invention find utility in multiplexing for detection and quantification of analytes.

"Intermediate product" refers to a product released from the reaction of the singlet oxygen-reactive group with singlet oxygen, as, for example, when the linker having a singlet oxygen-reactive group is reacted with singlet oxygen. As contemplated in the invention, an intermediate product includes, but is not limited to, an aldehyde, a ketone and/or other chemical entities that would be consistent with the scope of the invention. As contemplated by the invention, an intermediate product is subsequently converted to a converted product by reacting the intermediate product with the converting agent.

"Linker" refers to a structure that provides a connection between a binding compound, such as an antibody, and a releasable tag, such as an eTag. As set forth in this invention, a linker may be any compound which contains a singlet oxygen-reactive group. For example, a linker may include a thioether or any other structure that can be cleaved with a singlet oxygen. In a preferred embodiment of the invention, the linker is a thiother having the following structure:

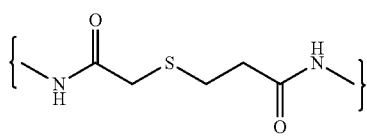

"Protein" refers to a polypeptide, usually synthesized by a biological cell, folded into a defined three-dimensional structure. Proteins are generally from about 5,000 to about 5,000,000 or more Daltons in molecular weight, more usually from about 5,000 to about 1,000,000 molecular weight, and may include posttranslational modifications, such acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, phosphorylation, prenylation, racemization, selenoylation, sulfation and ubiquitination, e.g., Wold, F., Post-translational Protein Modifications Perspectives and Prospects, pgs. 1-12 in Post-translational Covalent Modification of Proteins, B. C. Johnson, Ed., Academic Press, New York, 1983. Proteins include, by way of illustration and not limitation, cytokines or interleukins, enzymes such as, e.g., kinases, proteases, galactosidases and so forth, protamines, histones, albumins, immunoglobulins (e.g., such as antibodies), scleroproteins, phosphoproteins, mucoproteins, chromoproteins, lipoproteins, nucleoproteins, glycoproteins, T-cell receptors, proteoglycans, unclassified proteins, e.g., somatotropin, prolactin, insulin, pepsin, proteins found in human plasma, blood clotting factors, blood typing factors, protein hormones, cancer antigens, tissue specific antigens, peptide hormones, nutritional markers, tissue specific antigens and synthetic peptides.

"Releasable tag" refers to a chemical group or moiety that may be attached to a binding compound via a linker, whereby the linker contains a singlet oxygen-reactive group and the releasable tag is capable of being released via a singlet oxygen mediated cleavage whereby the releasable tag can then detected by a suitable detection system. According to a preferred embodiment of the invention, a preferred method of detection employs electrophoretic separation and employs an electrophorectic tag, an eTag. One preferred detection group of interest is a fluorescent group that can be readily detected during or after electrophoretic separation by illuminating the molecules with a light source in the excitation wavelength and detecting fluorescence emission from the irradiated molecules.

"Sample" refers to a quantity of material that is suspected of containing analytes of interest that are to be detected or measured. As used herein, the term includes a specimen (e.g., a biopsy or medical specimen) or a culture (e.g., microbiological culture). It also includes both biological and environmental samples. A sample may include a specimen of synthetic origin. Biological samples may be animal, including human, fluid, solid (e.g., stool) or tissue, as well as liquid and solid food and feed products and ingredients such as dairy items, vegetables, meat and meat by-products and waste. Biological samples may include materials taken from a patient including, but not limited to cultures, blood, saliva, CSF, pleural fluid, milk, lymph, sputum, semen, needle aspirates and the like. Biological samples may be obtained from all of the various families of domestic animals, as well as feral or wild animals. Environmental samples include environmental material such as surface matter, soil, water and industrial samples, as well as samples obtained from food and dairy processing instruments, apparatus, equipment, utensils, disposable and non-disposable items. These examples are not to be construed as limiting the sample types applicable to the present invention. In particular, biological samples include fixed biological specimens, such as patient biopsy specimens treated with a fixative, biological specimens embedded in paraffin (e.g., FFPE samples), frozen biological specimens, smears and the like.

"Singlet oxygen-reactive group" refers to a structure that is reactive with singlet oxygen. A preferred embodiment of the invention provides a linker which has a singlet oxygen-reactive group. According to a preferred embodiment, when the singlet oxygen-reactive group reacts with singlet oxygen, the linker is then cleaved resulting in the release of an intermediate product. In a preferred embodiment of the invention, the linker may be a thioether. In a preferred embodiment, the linker has the following structure:

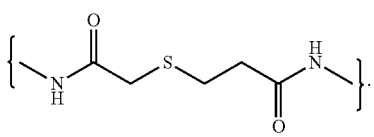

"Sufficient amount" refers to an amount and/or concentration of a converting agent sufficient to produce a desired effect, e.g., an amount sufficient to convert an intermediate aldehyde product to a measurable product.

It must be noted that, as used in the specification and the appended claims, the singular forms "a," "an" and "the" include plural referents unless the context clearly dictates otherwise.

Methods of the Invention

In one aspect, the invention is drawn to an enhanced method for detecting and/or quantifying at least one analyte in a sample.

In a particular embodiment, the method comprises the steps of:
  a. binding a binding compound to an analyte, the binding compound linked to a releasable tag through a linker, the linker containing a singlet oxygen-reactive group;
  b. releasing the releasable tag from the binding compound via a singlet oxygen mediated cleavage only if the binding compound has bound to the analyte and generating an intermediate product;
  c. reacting the intermediate product with at least one converting agent thereby producing at least one converted product; and
  d. detecting the at least one converted product and quantifying the at least one analyte.

Converting Agents, Intermediate Products and Converted Products

The converting agent can be any entity useful in carrying out the objects of the invention. The method uses a converting agent to convert an intermediate product, such as an aldehyde, to a converted product. A converting agent can be a reducing agent, an oxidizing agent, a Grignard reagent, hydrogen cyanide, an alcohol, an amine, thio (R—S—H) or bisulfite.

In one embodiment, the converting agent is a reducing agent. Examples of reducing agents, or processes, include sodium borohydride ($NaBH_4$), $NaB(CN)_3H$, $H_2$(Ni, Pt, or Pd), Clemmensen reduction Zn(Hg) or Wolff-Kishner reduction. Additional reducing agents are well known to one of skill in the art. In one embodiment, the converting agent is sodium borohydride ($NaBH_4$).

In other embodiments, the converting agent is an oxidizing agent. Examples of appropriate oxidizing agents include, but are not limited to, $NaOCl/H_2O_2$, $H_2O_2$/Air meta-chloroperoxybenzoic acid (m-CPBA) or OXONE (monopersulfate compound), $Ag(NH_3)_3$ and $K_2Cr_2O_7$. In still further embodiments, the converting agent is an alcohol or an amine. Example alcohols include, e.g., methanol or ethanol. Example amines include, e.g., R—$NH_2$, hydrazines (R—NH—$NH_2$) and hydrazides (R—CO—NH—$NH_2$) where the R can be any group, e.g., where R=H, $CH_3$, $C_2H_5$.

The converting agent can be added before the release reaction or after the release reaction. The converting agent is added in an amount or a concentration sufficient to convert the intermediate product to a converted product. One of skill in the art will understand that the sufficient amount or concentration depends upon the actual converting agents and upon reaction conditions. As an example, $NaBH_4$ may be used in a concentration of between about 50 to about 100 μg/ml and the converting reagent is added before the release of an eTag. In another embodiment, the final concentration of $NaBH_4$ is about 10 μg/ml and the converting agent is added after the release of the eTag.

The converted product that results may be different and depends upon the converting agent used: for example, the converted product may be an alcohol, an acid, an acetal, an imine, a cyanohydrin, an amine, a thioacetal or a sodium salt of organic sulfite. In a preferred embodiment, the converted product is an alcohol. In a preferred embodiment, the converted product is an acid.

Releasable Tags

The releasable tag may be any chemical group or moiety that may be attached to a binding compound via a linker, and will depend on the application and reaction conditions. In one embodiment, the releasable tag is an eTag as described in U.S. Pat. Nos. 6,770,439 and 7,105,308, each of which is incorporated by reference herein, including any drawings.

A releasable tag is preferably a water-soluble organic compound that is stable with respect to the active species, especially singlet oxygen, and that includes a detection or reporter group. Otherwise, the releasable tag may vary widely in size and structure. In one aspect, the releasable tag has a molecular weight in the range of from about 50 to about 2500 daltons, more preferably, from about 50 to about 1500 daltons. Preferred structures of the releasable tag are described more fully herein, as well as in U.S. Pat. Nos. 6,770,439 and 7,105,308, each of which is incorporated by reference herein including any drawings. The releasable tag may comprise a detection group for generating an electrochemical, fluorescent or chromogenic signal. A releasable tag may also be detected by mass, and in embodiments employing detection by mass, the releasable tag may not have a separate moiety for detection purposes.

A single releasable tag may be chosen or many releasable tags may be chosen. Individual releasable tags may be selected so that each has unique separation characteristic and/or unique optical properties with respect to the other release tags that may be chosen. In one embodiment, releasable tags are chosen based upon different chromatographic or electrophoretic separation characteristics such as retention time under sets of standard separation conditions conventional in the art, e.g. voltage, column pressure, column type, mobile phase, electrophoretic separation medium or the like. In another aspect, optical properties may be used to differentiate releasable tags from one another. Optical properties that may be useful for distinguishing releasable tags include, but are not limited to, fluorescence properties, such as emission spectra, fluorescent lifetime, fluorescent intensity at a given wavelength or band of wavelengths or the like. Preferably, the fluorescent property is fluorescent intensity. For example, if a plurality of releasable tags is used, each releasable tag of the plurality may have the same fluorescent emission properties but then differ, one from another, by virtue of a unique retention time. Alternatively, one or two or more of the releasable tags of a plurality may have identical retention times yet have unique fluorescent properties, e.g. spectrally resolvable emission spectra, so that all the members of the plurality are distinguishable by the combination of molecular separation and fluorescence measurement.

Preferably, releasable tags are detected by electrophoretic separation and the fluorescence of a detection group. In some embodiments, releasable tags having substantially identical fluorescent properties have different electrophoretic mobilities so that distinct peaks in an electropherogram are formed under separation conditions. Preferably, pluralities of releasable tags are separated by a conventional capillary electrophoresis apparatus, either in the presence or absence of a conventional sieving matrix. Exemplary capillary electrophoresis apparatus include Applied Biosystems (Foster City, Calif.) models 310, 3100, 3130, 3700 and 3730; Beckman (Fullerton, Calif.) model P/ACE MDQ; Amersham Biosciences (Sunnyvale, Calif.) MegaBACE 1000 or 4000 and the like. Electrophoretic mobility is proportional to $q/M^{2/3}$, where q is the charge on the molecule and M is the mass of the molecule. Desirably, the difference in mobility under the conditions of the determination between the closest electrophoretic labels will be at least about 0.001, usually 0.002, more usually at least about 0.01 and may be 0.02 or more. Preferably, in such conventional apparatus, the electrophoretic mobilities of releasable tags of a plurality differ by at least one percent, and more preferably, by at least a percentage in the range of from 1 to 10 percent.

Preferably, the releasable tag generates a fluorescent signal. Exemplary fluorescent dyes for use with the invention include water-soluble rhodamnine dyes, fluoresceins, 4,7-dichlorofluoresceins, benzoxanthene dyes and energy transfer dyes, disclosed in the following references: Handbook of Molecular Probes and Research Reagents, $8^{th}$ ed., (Molecular Probes, Eugene, 2002); Lee et al, U.S. Pat. No. 6,191,278; Lee et al, U.S. Pat. No. 6,372,907; Menchen et al, U.S. Pat. No. 6,096,723; Lee et al, U.S. Pat. No. 5,945,526; Lee et al, Nucleic Acids Research, 25: 2816 2822 (1997); Hobb, Jr., U.S. Pat. No. 4,997,928; Khanna et al., U.S. Pat. No. 4,318,846; Reynolds, U.S. Pat. No. 3,932,415; Eckert et al, U.S. Pat. No. 2,153,059; Eckert et al, U.S. Pat. No. 2,242,572; Taing et al, International patent publication WO 02/30944 and the like.

In one embodiment, the releasable tag may be represented by the formula "(M, D)" where M is a mobility-modifying moiety and D is a detection moiety. The notation "(M, D)" is used to indicate that the ordering of the M and D moieties may be such that either moiety can be attached to and adjacent to the linker. That is, "(M, D)" designates a releasable tag of either of two forms: "M-D" or "D-M." Detection moiety, D, may be a fluorescent label or dye, a chromogenic label or dye, an electrochemical label or the like. Preferably, D is a fluorescent dye.

The size and composition of a mobility-modifying moiety, M, can vary from a bond to about 100 atoms in a chain, usually not more than about 60 atoms, more usually not more than about 30 atoms, where the atoms are carbon, oxygen, nitrogen, phosphorous, boron and sulfur. Generally, when other than a bond, the mobility-modifying moiety has from about 0 to about 40, more usually from about 0 to about 30 heteroatoms, which in addition to the heteroatoms indicated above may include halogen or other heteroatoms. The total number of atoms other than hydrogen is generally fewer than about 200 atoms, usually fewer than about 100 atoms. Where acid groups are present, depending upon the pH of the medium in which the mobility-modifying moiety is present, various cations may be associated with the acid group. The acids may be organic or inorganic, including carboxyl, thionocarboxyl, thiocarboxyl, hydroxamic, phosphate, phosphite, phosphonate, phosphinate, sulfonate, sulfinate, boronic, nitric and nitrous, etc. For positive charges, substituents include amino (including ammonium), phosphonium, sulfonium and oxonium, etc., where substituents are generally aliphatic of from about 16 carbon atoms, the total number of carbon atoms per heteroatom and usually will be less than about 12, usually less than about 9. The side chains include amines, ammonium salts, hydroxyl groups, including phenolic groups, carboxyl groups, esters, amides, phosphates and heterocycles. M may be a homo-oligomer or a hetero-oligomer having different monomers of the same or different chemical characteristics, e.g., nucleotides and amino acids.

M may also comprise polymer chains prepared by known polymer subunit synthesis methods. Methods of forming selected-length polyethylene oxide-containing chains are well known, e.g. Grossman et al, U.S. Pat. No. 5,777,096, which is incorporated by reference herein including any drawings. It can be appreciated that the methods, which involve coupling of defined-size, multi-subunit polymer units to one another, directly or via linking groups, are applicable to a wide variety of polymers, such as polyethers (e.g., polyethylene oxide and polypropylene oxide), polyesters (e.g., polyglycolic acid or polylactic acid), polypeptides, oligosaccharides, polyurethanes, polyamides, polysulfonamides, polysulfoxides, polyphosphonates and block copolymers thereof, including polymers composed of units of multiple subunits linked by charged or uncharged linking groups. In addition to homopolymers, the polymer chains used in accordance with the invention include selected-length copolymers, e.g., copolymers of polyethylene oxide units alternating with polypropylene units. As another example, polypeptides of selected lengths and amino acid composition (i.e., containing naturally occurring or man-made amino acid residues) as homopolymers or mixed polymers may be used.

In another embodiment, M may be synthesized from smaller molecules that have functional groups that provide for linking of the molecules to one another, usually in a linear chain. Such functional groups include carboxylic acids, amines and hydroxy- or thiol-groups. In accordance with the present invention the charge-imparting moiety may have one or more side groups pending from the core chain. The side groups have a functionality to provide for linking to a label or to another molecule of the charge-imparting moiety. Common functionalities resulting from the reaction of the functional groups employed are exemplified by forming a covalent bond between the molecules to be conjugated. Such functionalities are disulfide, amide, thioamide, dithiol, ether, urea, thiourea, guanidine, azo, thioether, carboxylate and esters and amides containing sulfur and phosphorus such as, e.g., sulfonate, phosphate esters, sulfonamides, thioesters, etc. and the like.

Binding Compounds

The releasable tag is linked to a binding compound. The binding compound can be any number of molecules to which releasable tags can be directly or indirectly attached, where the binding compound is capable of specifically binding to an analyte. For example, binding compounds may include, but are not limited to, antibodies, antibody binding compositions, peptides, proteins, such as secreted proteins and orphan secreted proteins, nucleic acids, and organic molecules having a molecular weight of up to 1000 daltons and consisting of atoms selected from the group consisting of hydrogen, carbon, oxygen, nitrogen, sulfur and phosphorus.

In one embodiment, the binding compound is an antibody. Such compositions are readily formed from a wide variety of commercially available antibodies and can be used with both monoclonal and polyclonal antibodies. As an example, antibodies specific for epidermal growth factor receptors are disclosed in the following patents which are incorporated herein by reference, including any drawings: U.S. Pat. Nos. 5,677,171; 5,772,997; 5,968,511; 5,480,968 and 5,811,098.

Linkers

A linker refers to a structure that provides a connection between a binding compound, such as an antibody, and a releasable tag, such as an eTag. As set forth in this invention, a linker may be any compound which contains a singlet oxygen-reactive group. For example, a linker may include a thioether or any other structure that can be cleaved with a singlet oxygen. In a preferred embodiment of the invention, the linker is a thiother having the following structure:

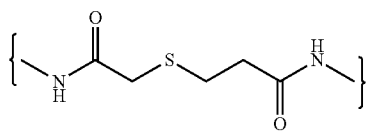

When using an eTag linked to a binding compound, e.g., an antibody, the linker may or may not contribute a linking-group "residue" to the releasable tag. For example, where the linker is a chemical group or chain which is cleaved internally or immediately adjacent to the releasable tag, cleavage of the linker will leave a residual mass and, possible charge contribution to the releasable tag. In general, this contribution will be relatively small, and the same for each different released e-tag (assuming a common linking group within the probe set).

Singlet Oxygen Mediated Release

For singlet oxygen, one may use various sensitizers, such as squarate derivatives. See, for example, Ullman, et al., Proc. Natl. Acad. Sci. USA 91, 5426-5430 (1994). Examples of combinations that find use in this invention may be found in U.S. Pat. Nos. 5,536,498 and 5,536,834 and references cited therein; H. H. Wasserman and R. W. Murray. Singlet Oxygen. Academic Press, New York (1979) and A. L. Baumstark, Singlet Oxygen, Vol. 2, CRC Press Inc., Boca Raton, Fla. 1983. Other cleavage mechanisms may be found in WO99/64519; WO99/13108; WO98/01533 and WO97/28275, each of which are incorporated by reference herein, including any drawings.

Samples

In a preferred embodiment, the sample is a biological sample. The biological sample can be any sample that may or may not contain an analyte of interest. Biological samples specifically may be almost anything of interest obtained from a patient, such as a human, including but not limited to blood, biological fluids, cells, plasma and most any other tissues. Examples of biological samples include, without limitation, CSF, urine, sputum or fresh tissue. A biological sample may be immediately obtained or may be preserved, or fixed, for analysis at a later time. Methods of fixation can be any that are well-known to one skilled in the art. Such methods of fixation include, but are not limited to, FFPE tissue samples, frozen tissue samples or any other fixed tissue that is known to one skilled in the art. In a preferred embodiment, the sample is an FFPE tissue sample.

Samples containing analytes of interest may come from a wide variety of sources including cell cultures, animal or plant tissues, microorganisms, patient biopsies or the like. Samples are prepared for assays of the invention using conventional techniques, which may depend on the source from which a sample is taken. Guidance for preparing cell membranes for analysis can be found in standard treatises, such as Sambrook et al, Molecular Cloning, Second Edition (Cold Spring Harbor Laboratory Press, New York, 1898); Innis et al, editors, PCR Protocols (Academic Press, New York, 1990); Berger and Kimmel, "Guide to Molecular Cloning Techniques," Vol. 152, Methods in Enzymology (Academic Press, New York, 1987); Ohlendieck, K. (1996). Protein Purification Protocols; Methods in Molecular Biology, Humana Press Inc., Totowa, N.J. Vol 59: 293 304; Method Booklet 5, "Signal Transduction" (Biosource International, Camarillo, Calif., 2002) or the like. For mammalian tissue culture cells, or like sources, samples of target membrane-associated analytes may be prepared by conventional cell lysis techniques (e.g. 0.14 M NaCl, 1.5 mM $MgCl_2$, 10 mM Tris-Cl (pH 8.6), 0.5% Nonidet P-40 and protease and/or phosphatase inhibitors as required). For biopsies and medical specimens: see, e.g., Bancroft J D & Stevens A, eds. Theory and Practice of Histological Techniques (Churchill Livingstone, Edinburgh, 1977) or Pearse, Histochemistry. Theory and applied. $4^{th}$ ed. (Churchill Livingstone, Edinburgh, 1980).

Analytes

In a preferred embodiment, the analyte is a biological molecule of interest. The analyte may be at least one protein. The analyte may also be at least one interacting set of proteins, such as, without limitation, at least one oligomer or at least one dimer. The analyte may also be at least one nucleic acid, such as a nucleic acid of interest.

The analyte may be at least one protein whose expression could be related to the prognosis or diagnosis of a disease such as cancer. Non-limiting examples of analytes associated with a disease such as cancer include: CD20, CD19, CD30, CD3, GD2, Lewis-Y, 72 kd glycoprotein (gp72, decay-accelerating factor, CD55, DAF, C3/C5 convertases), CO17-1A (EpCAM, 17-1A, EGP-40), TAG-72, CSAg-P (CSAp), 45 kd glycoprotein, HT-29 ag, NG2, A33 (431 kd gp), 38 kd gp, MUC-1, CEA, EGFR (HER1), HER2, HER3, HER4, HN-1 ligand, CA125, syndecan-1, Lewis X, PgP, FAP stromal Ag (fibroblast activation protein), EDG receptors (endoglin receptors), ED-B, c-Met, laminin-5 (gamma2), cox-2 (+LN-5), PgP (P-glycoprotein), alphaVbeta3 integrin, alphaVbeta5 integrin, uPAR (urokinase plasminogen activator receptor), endoglin (CD105), folate receptor osteopontin (EDG 1,3), p97 (melanotransferrin), farnesyl transferase or a molecule in an apoptotic pathway (e.g., a death receptor, fas, caspase or bcl-2) or a lectin.

Other non-limiting examples of protein and chemical analytes that may be of interest include chemokines and cytokines and their receptors. Cytokines as used herein refers to any one of the numerous factors that exert a variety of effects on cells, for example inducing growth or proliferation. Non-limiting examples include interleukins (IL), IL-2, IL-3, IL-4 IL-6, IL-10, IL-12, IL-13, IL-14 and IL-16; soluble IL-2 receptor; soluble IL-6 receptor; erythropoietin (EPO); thrombopoietin (TPO); granulocyte macrophage colony stimulating factor (GM-CSF); stem cell factor (SCF); leukemia inhibitory factor (LIF); interferons; oncostatin M(OM); the immunoglobulin superfamily; tumor necrosis factor (TNF) family, particularly TNF-.alpha.; TGF.beta.; IL-1.alpha and the vascular endothelial growth factor (VEGF) family and their receptors, particularly VEGF (also referred to in the art as VEGF-A), VEGF-B, VEGF-C, VEGF-D and placental growth factor (PLGF).

Membrane-associated analytes may include molecules that form dimeric or oligomeric complexes. For example, receptors involved in signal transduction are of particular interest, including, but not limited to, enzyme-associated receptors and G-protein coupled receptors. Enzyme-associated receptors of interest include several types having intrinsic enzymatic activities, including those with tyrosine kinase activity, tyrosine phosphatase activity, guanylate cyclase activity and serine/threonine kinase activity. Examples of tyrosine kinase-associated receptors include, but are not limited to, the Her receptor family, insulin receptor, IGF-1 receptor, PDGF receptors, FGF receptors, VEGF receptors, HGF and SC receptors, the neurotrophin receptor family and NGF receptor. Examples of tyrosine phosphatase-associated receptors include, e.g., CD45 protein. Examples of guanylate cyclase-associated receptors include, e.g., the natriuretic peptide receptors. Examples of serine/threonine kinase-associated receptors include, e.g., activin receptor and transforming growth factor beta (TGF-.beta.) receptors.

In another aspect, the invention is drawn to a method for detecting and quantifying at least one analyte in a sample, the method comprising:

a. binding at least one binding compound linked to a releasable tag through a linker, the linker containing a singlet oxygen-reactive group;

b. reacting the labeled binding element with at least one converting agent;

c. releasing the releasable tag from the binding compound only if the binding element has bound to the analyte, via a singlet oxygen mediated cleavage and producing at least one intermediate product which can be converted to at least one converted product and d. detecting and quantifying the converted product and quantifying the at least one analyte.

In a particular embodiment, the linker is a thioether. In a particular embodiment, the thioether is a compound having the following structure:

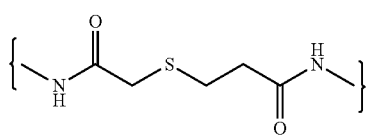

In a particular embodiment, detection and/or quantification of the converted product occurs by electrophoresis. In a particular embodiment, the electrophoresis is capillary electrophoresis. In a particular embodiment, the releasable tag comprises a signal or reporter molecule. In a preferred embodiment, the releasable tag comprises an eTag. In a particular embodiment, the signal or reporter molecule is a fluorescent molecule. In a preferred embodiment, the binding compound comprises an antibody, a protein, an aptamer, a nucleic acid or a peptide nucleic acid. In a preferred embodiment, the binding compound comprises an antibody. In a preferred embodiment, the releasable tag comprises an eTag and the binding compound comprises an antibody.

The converting agent or the converted product can be any entity useful in carrying out the objects of the invention. In a preferred embodiment, the converting agent comprises a reducing agent, an oxidizing reagent, a Grignard reagent, hydrogen cyanide, an alcohol, an amine, thiol (R—S—H) or bisulfite (NaHSO3). In a preferred embodiment, the converting agent is a reducing agent. In a preferred embodiment, the reducing agent is sodium borohydride (NaBH$_4$). In a preferred embodiment, the converting agent is an oxidizing agent. In a preferred embodiment, the oxidizing agent is NaOCl/H$_2$O$_2$, H$_2$O$_2$/air, meta-chloroperoxybenzoic acid (m-CPBA) or OXONE® (monopersulfate compound). In a preferred embodiment, the oxidizing agent is m-CPBA. In a preferred embodiment, the converted product is an alcohol, an acid, an acetal, an imine, cyanohydrin, an amine, a thioacetal or a sodium salt of an organic sulfite. In a preferred embodiment, the converted product is an alcohol. In a preferred embodiment, the converted product is an acid.

In a preferred embodiment, the sample is a biological sample. The biological sample can be any sample that may or may not contain an analyte of interest. Biological samples specifically may be almost anything of interest obtained from a patient, such as a human, including but not limited to blood, biological fluids, cells, plasma and most any other tissues. Examples of biological samples include, without limitation, CSF, urine, sputum or fresh tissue. A biological sample may be immediately obtained or may be preserved, or fixed, for analysis at a later time. Methods of fixation can be any that are well-known to one skilled in the art. Such methods of fixation include, but are not limited to, tissue that is FFPE tissue, frozen tissue samples or any other fixation method that is known to one skilled in the art. In a preferred embodiment, the sample is an FFPE tissue sample.

In a preferred embodiment, the analyte is a biological molecule of interest. In a preferred embodiment, the analyte is at least one protein. In a preferred embodiment, the analyte is at least one interacting set of proteins, such as, without limitation, at least one oligomer or at least one dimer. In a preferred embodiment, the analyte is at least one nucleic acid, such as, without limitation, a nucleic acid of interest. In a preferred embodiment, the analyte may be used as a biological marker for prediction or prognosis of disease in a patient in need thereof.

EXAMPLES

Below are examples of specific embodiments for carrying out the present invention. The examples are offered for illustrative purposes only and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of organic chemistry, protein chemistry, biochemistry, recombinant DNA techniques and pharmacology within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences,* 18th Edition (Easton, Pa.: Mack Publishing Company, 1990) and Carey and Sundberg *Advanced Organic Chemistry* 3$^{rd}$ Ed. (Plenum Press) Vols A and B (1992).

Example 1

General Practice: eTag Assay

Example 1 sets forth a general practice for the eTag assay. Monoclonal antibodies (mAbs) conjugated to either releasable tags or cleavage agents ("molecular scissors") recognize and bind a specific analyte at different epitopes, as set forth in the examples (see also, for example, U.S. Pat. No. 7,105,308 which is incorporated by reference herein, including any drawings). The "eTag antibody conjugate" is composed of an analyte-specific mAb conjugated to a fluorescent releasable tag of unique mass-charge ratio. The "molecular scissor" is composed of a biotin-conjugated mAb linked to a photosensitizer molecule via streptavidin. Upon photo-activation, this molecular scissors complex generates a reactive singlet oxygen that specifically and precisely cleaves neighboring (~200 Å radius) thioether bonds [Corey, E. J. and C. Ouannés, Intermédiaire dans L'oxydation de Benzylalcoyl Sulfures par L'oxygène Singulet Tetrahedron Letters, 1976. 17(47): p. 4263-4266].

When the eTag antibody conjugate and the molecular scissors-mAb conjugate are bound to the same analyte or to an analyte in close proximity, the reactive singlet oxygen preferentially cleaves the proximate thioether bond linking the releasable tag and mAb due to the short half life of singlet oxygen (<4 µs), thereby releasing the releasable tag [see, e.g., Kochevar, I. E. and R. W. Redmond, Photosensitized Production of Singlet Oxygen. Methods Enzymol, 2000. 319: p. 20-8.; Skovsen, E., et al., Lifetime and Diffusion of Singlet Oxygen in a Cell. J Phys Chem B, 2005. 109(18): p. 8570-3].

Following cleavage, releasable tags are collected, converted, then separated and quantified by capillary electrophoresis (CE). Because of their distinct mobilities, multiplex assays are possible, as all releasable tag species are readily differentiated from one another following separation by CE and subsequent quantitation.

Example 2

Specific eTag Assay Using Converting Agent Sodium Borohydride (NaBH$_4$)

eTag antibody conjugation: eTag releasable tags were conjugated to relevant antibodies using standard conjugation chemistry with N-hydroxysuccinimide (NHS) esters (see-*Bioconjugate Techniques*; Hermanson, G. T.; Academic Press: San Diego, 1996). Conjugated antibodies were purified using size-exclusion chromatography (Sephadex G-25) and preservatives and stabilizers were added.

Molecular scissors antibody coupling: Two reagents were prepared. The first reagent is a biotin-linked antibody that recognizes a particular epitope of the target molecule (see-__ *Bioconjugate Techniques*; Hermanson, G. T.; Academic Press: San Diego, 1996). The second reagent is the streptavidin-scissors conjugate. The scissors are photosensitizer molecules that bind to the biotin-antibody reagent in a subsequent reaction.

Capillary Electrophoresis Mobility Markers: MF, ML and F: Capillary electrophoresis mobility markers were used to demarcate the beginning (MF) and end (ML) of the electropherogram containing the peaks from the assay-derived VeraTag reporter and quantification marker (F). VeraTag eTag Informer™ software uses the relative time of migration of these CE markers to identify the relative size of migration of each releasable tag.

Quantification Standard: Fluorescein: A quantification standard is used as an internal control of VeraTag releasable tag recovery and electrokinetic injection variation during capillary electrophoresis of every sample. For these assays, the quantification standard is fluorescein (F). Illumination reactions (cleavage of VeraTag releasable tag by photoactivation of the molecular scissors) are performed in the presence of a known amount of the F quantification marker. Specifically, 3 pM fluorescein was used. The relative ratio between the signal from the recovered releasable tag and the quantification marker adjusts for differential recovery and injection, thus allowing for comparison of results across assays.

Specifically, the CE fluorescence signal intensity of a releasable tag, or the peak area ($PA_{VeraTag}$), is given in relative fluorescent units (signal height) integrated across time (RFU-S/S). The relative peak area ($RPA_{VeraTag}$) is measured by normalizing the releasable tag peak area ($PA_{VeraTag}$) with respect to the internal fluorescein standard of known concentration ($PA_F$), and is therefore proportional to the initial concentration of the analyte being measured.

Reducing Agent for Peak Conversion: Sodium Borohydride: After illumination, intermediate products are reduced to a quantifiable form by the addition of a converting agent of sodium borohydride. A fresh solution of 50 µg/mL of NaBH$_4$ was prepared. The NaBH$_4$ was added to the appropriate sample at a final concentration of 10 µg/mL and mixed well. The sample/NaBH$_4$ solution mix was incubated at room temperature for 5 minutes. An aliquot of the sample, about 10 µL, was added to the appropriate wells of the CE plate. The converted product was quantified. NaBH$_4$ was also added before starting the illumination and with higher concentration at about 50 to 100 µg/ml to each sample.

General Data Analyses: Multiple steps occur to process data to a final reportable value: calculation of relative peak area, normalization for tumor content and illumination buffer volume and, lastly, batch normalization.

Relative Peak Area: Signals from two concomitantly run CE markers (MF and ML) are used to demarcate the relevant region of the electropherogram and to locate the assay-specific peaks from the releasable tags (i.e., the release peak and the converted peak). Once identified, the signal intensity, measured in relative fluorescence units (RFU), is calculated for each VeraTag reporter as the area of the electropherogram peak by integrating the signal intensity (height) across time (see, for example, FIG. 8). The Peak Area for each releasable tag is then normalized for within assay variation using an internal standard of known concentration (i.e., 3 pM fluorescein). This value is reported as Relative Peak Area (RPA) (Tian, H., et al., Multiplex mRNA Assay using Electrophoretic Tags for High-throughput Gene Expression Analysis. Nucleic Acids Res, 2004. 32(16): p. e126). Signal intensity is proportional to the initial concentration of the corresponding target analyte. In addition, quality checks of the signal level are applied to reject poor quality results.

Example 3

Specific eTag Assay Using Converting Agent m-CPBA

An assay was carried out using methods similar to those set forth in Example 2 but involving an oxidizing agent as a converting agent. Specifically, m-CPBA was used as a converting agent.

Reagents: (i) Biotin-BSA Pro 14:10 uM; (ii) Biotin-BSA Pro 11:10 uM; (iii) Molecular Scissors (latex beads coated with pthalocyanine conjugated to strepavidin, 200 µg/ml); (iv) Stock of m-CPBA: 100 mM; (v) Buffer H:50 mM Tris, 1 mg/ml Dextran, 1 mg/ml BSA, 2 mg/ml ZD3-14 and 1 mM EDTA); (vi) Wash Buffer: (50 mM Tris, 2 mg/ml deoxycholate and 20 uM HABA).

Instrumentation:

(i) MultiScreen DVPP Filter plates, 0.22 um (Fisher/Millipore,cat. #MAGVN2250); (ii) Millipore Vacuum Manifold (Millipore, cat. #MAVM 09660R) operating at 10 in Hg; (iii) Titer Plate Shaker (Labline, Inc. model 4625); (iv) LED array (Aclara Part #MGRM276); (v) ABI 96 well plates (cat. #N8010560); (vi) ABI 3100 CE instrument Assays were performed in Buffer H. 20 ul of 10 uM Biotin-BSA-releasable tag in Buffer H was incubated with 20 ul of 200 µg/ml of Molecular scissors prepared in 50 mM Tris. The incubation was done for 30 min on a shaker in the regular filter plate. After incubation the solution was drained using a vacuum and washed 2 times with wash buffer. Next, 50 ul of Illumination buffer (Illumination Buffer: 20 µM A160, 20 µM A315, 5 µM HABA) was added, (Containing Markers A160 (M1), A315 (M2)). Illumination of the mixture was for 10 min. Next, 20 ul was transferred to a CE plate.

For 1000 excess, 5 ul of 250 uM of m-CPBA was added in 20 ul of the released tag mixture, and then readied for CE. For 10000 excess, 5 ul of 2.5 mM of m-CPBA was added in 20 ul of the released tag mixture and then readied for CE. Reactions were carried for 1 hrs, 2 hrs and 4 hrs and overnight.

Figure 7A:
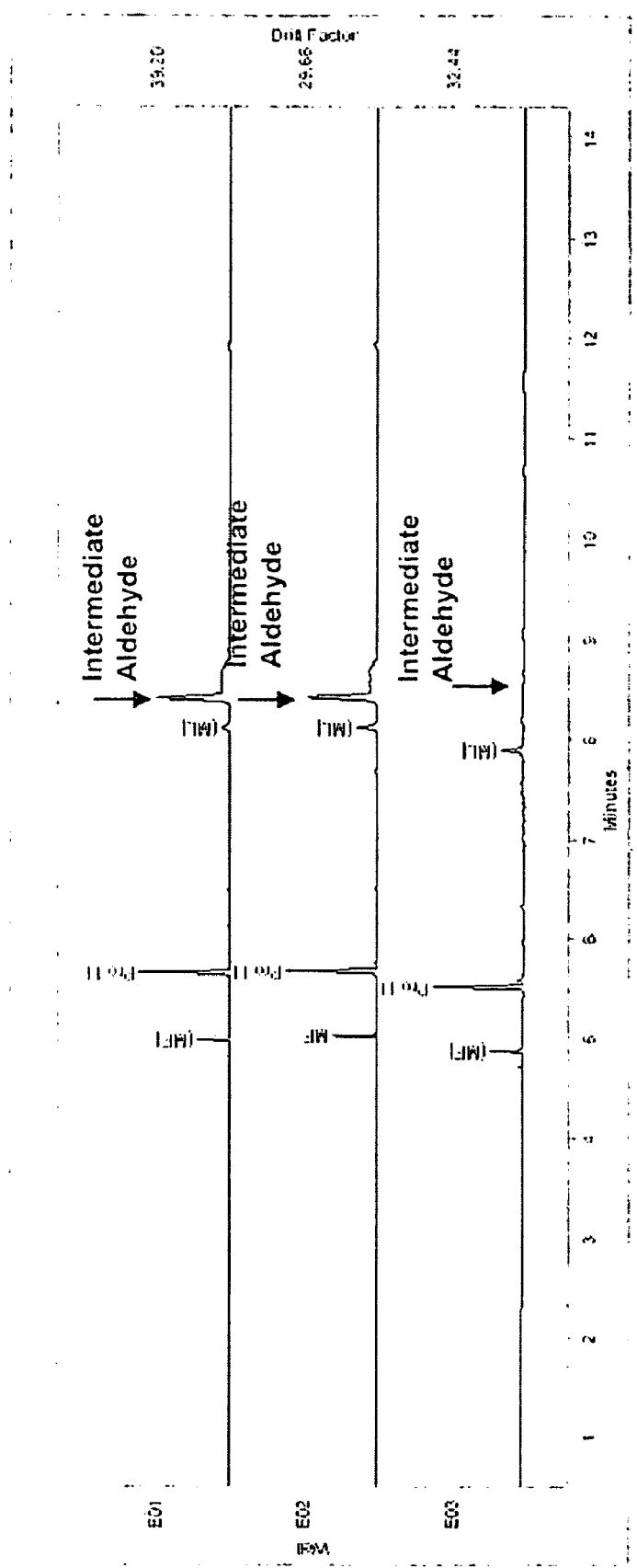
FIG. 7A shows three electropherograms resulting from a four hour run with Pro11. The top electropherogram shows results without the addition of a converting agent, the middle shows the results with the addition of 1000 excess m-CPBA and the bottom shows the addition of 10000 excess m-CPBA. The converting agent was added after illumination (see FIG. 1 and FIG. 2). The releasable tag is shown here as Pro 11. The x-axis shows relative movement and the y-axis shows the height of the peak as described example (see, for example, Example 4 et seq).
Figure 7B:
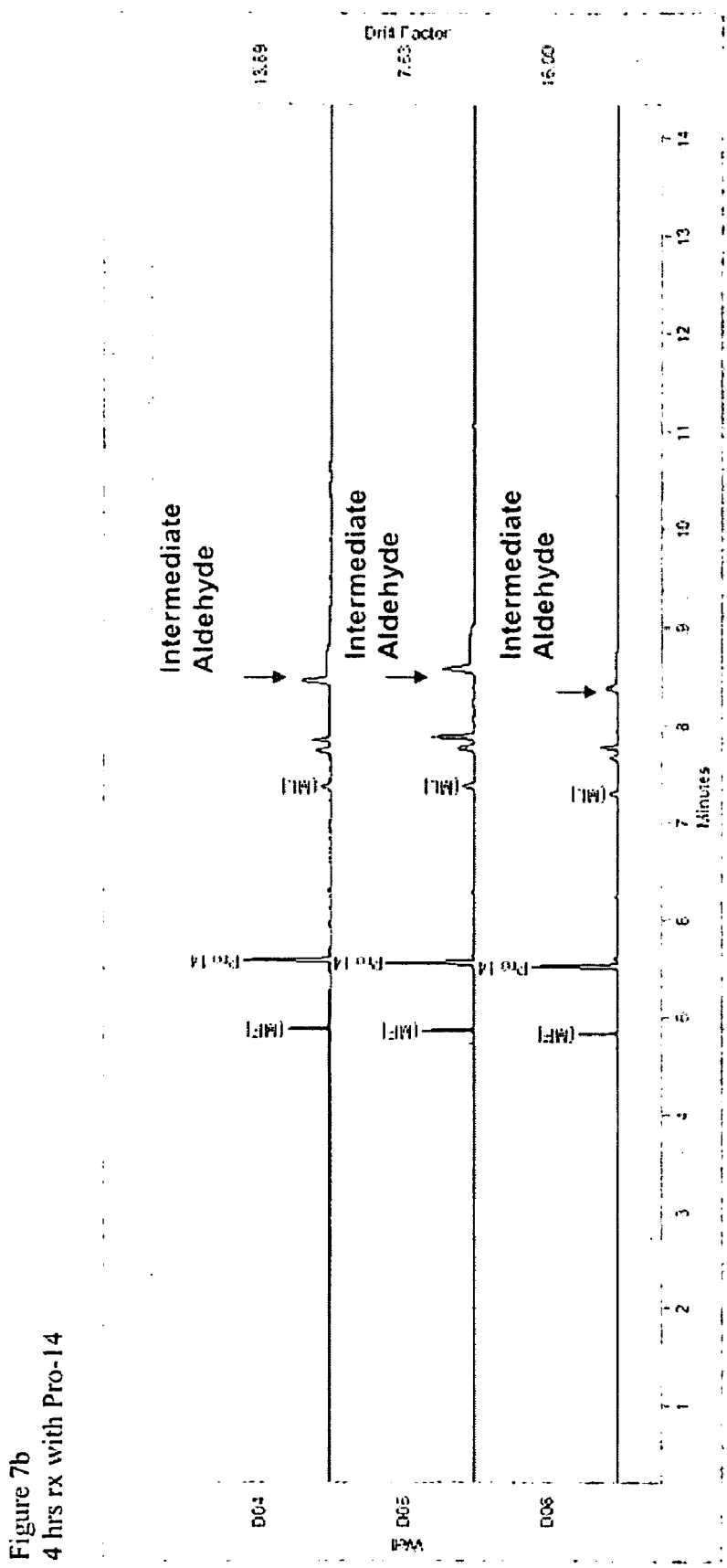
FIG. 7B shows three electropherograms resulting from a four hour run with Pro14. The top electropherogram shows results without the addition of a converting agent, the middle shows the results with the addition of 1000 excess m-CPBA and the bottom shows the addition of 10000 excess m-CPBA. The converting agent was added after illumination (see FIG. 1 and FIG. 2). The releasable tag is here shown as Pro 14. The x-axis shows time in minutes and the y-axis shows the height of the peak. MF and ML represent internal control peaks, specifically the first migration marker (MF) and the last migration marker (ML). Formation of the converted product peak leads to an enhanced ability to detect and/or quantify the analyte.

No difference in the amount of intermediate product, an aldehyde, or converted product was seen after 1 or 2 hours (data not shown). As shown in FIG. 7, conversion of the intermediate aldehyde product to converted product (released peak) occurred after 4 hours of oxidation. With these conditions we observed an approximate 3 fold increase in peak area after oxidation with m-CPBA (see, Example 2, above).

Example 4

Preparation of an Intermediate Product, an Aldyde: Pro4-de Novo-CHO

A series of synthetic reactions were performed in order to characterize reaction of an intermediate product a converting agent to form a converted product, e.g., an alcohol or an imine or an acid (see, Example 6 et seq).

A synthetic aldehyde, Pro4-de novo CHO, was prepared as follows. To a stirred solution of 5-carboxyfluorescein (5-FAM) (190 mg, 0.51 mmol) in anhydrous N,N-dimethylformamide (DMF (5 mL) were added N-hydroxysuccinimide (NHS) (77 mg, 0.67 mmol) and 1,3-dicyclohexylcarbodiimide (DCC) (126 mg, 0.61 mmol). After approximately 5 minutes, a white solid (dicyclohexylurea) started forming. The reaction mixture was stirred overnight under nitrogen. Thin layer chromatography (TLC) (40:9:1 $CH_2Cl_2$—$CH_3OH$-water) indicated complete disappearance of the starting material. The mixture was then filtered, and the filtrate was added dropwise to a stirred solution of ethylene diamine (46 mg, 0.77 mmol) in DMF (3 mL). A solid was obtained. As evident from TLC, the reaction was complete instantaneously. This reaction mixture was subsequently treated with glyoxylic acid NHS ester prepared below.

To a stirred solution of glyoxylic acid monohydrate (431 mg, 4.56 mmol) in anhydrous DMF (5 mL) were added NHS (563 mg, 4.89 mmol) and DCC (1.00 g, 4.85 mmol). A white solid (dicyclohexylurea) formed immediately. As the reaction was exothermic, the flask was cooled in an ice-bath for a while (approximately 5 minutes). The reaction mixture was then stirred under nitrogen at room temperature for approximately 1 hour. The solid was filtered off and washed with DMF. The filtrate (containing glyoxylic acid NHS ester) was then added to the reaction mixture obtained above. After stirring the mixture for approximately 5 minutes, a clear solution was obtained. TLC revealed completion of the reaction. The solvent was removed under reduced pressure. Flash chromatography (20:1 and 15:1 $CH_2Cl_2$—$CH_3OH$ followed by 20:1, 15:1 and 12:1 $CH_2Cl_2$—$CH_3OH$ containing 1% acetic acid) provided the desired Pro4-de novo-CHO (132 mg, 55%). The mass spectrum was in agreement with the assigned structure.

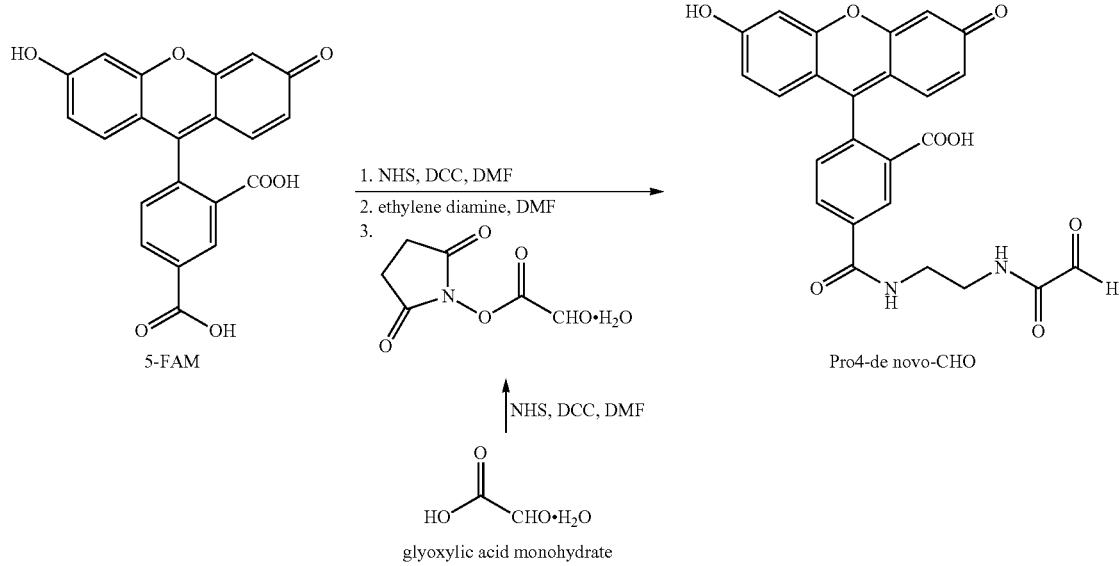

Example 5

Conversion of Intermediate Product Pro4-de Novo-CHO to a Converted Product, an Alcohol, with a Converting Agent, NaBH$_4$

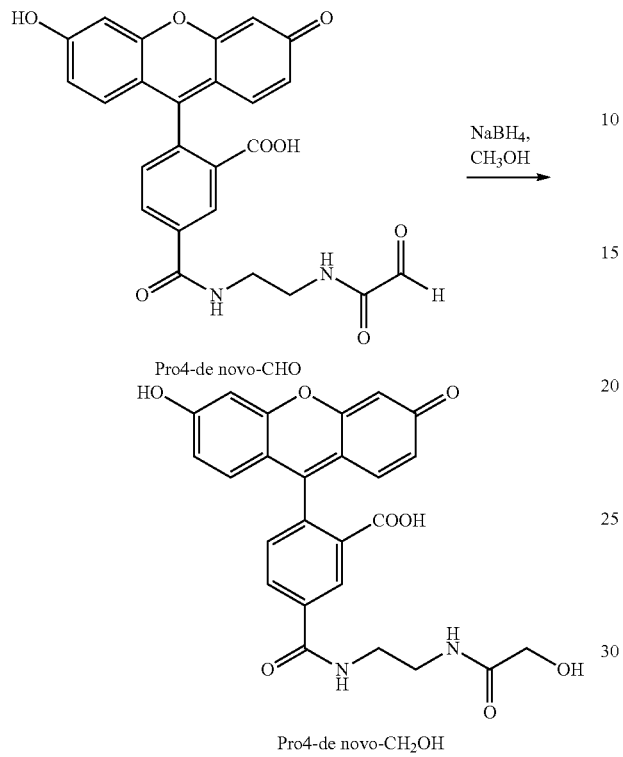

To the stirred solution of the intermediate product, Pro4-de novo-CHO (32 mg, 0.067 mmol) in CH$_3$OH (2 mL) was added a converting agent, sodium borohydride (NaBH$_4$) (19 mg, 0.50 mmol). Evolution of a gas (H$_2$) was observed, and the reaction solution turned dark red. The solution was then acidified with 1 N aqueous HCl (0.5 mL). The resulting light-yellow solution's pH was now approximately 3. TLC (40:9:1 CH$_2$Cl$_2$—CH$_3$OH-water) indicated completion of the reaction. Removal of the solvent under reduced pressure afforded the converted product, Pro4-de novo-CH$_2$OH, an alcohol, as a yellow solid. The structural assignment was made on the basis of its mass spectrum.

Example 6

Conversion of an Intermediate Product, Pro4-de Novo-CHO to a Converted Product, an Imine, with the Converting Agent Isopropylamine

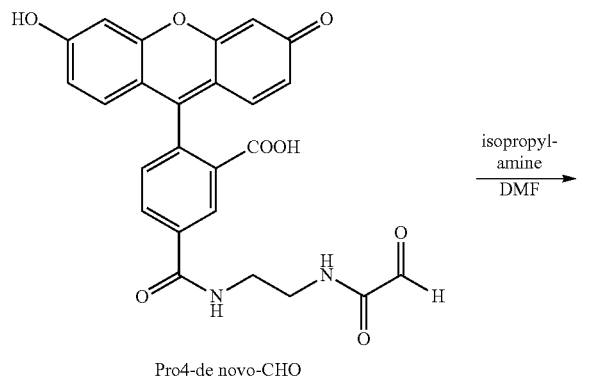

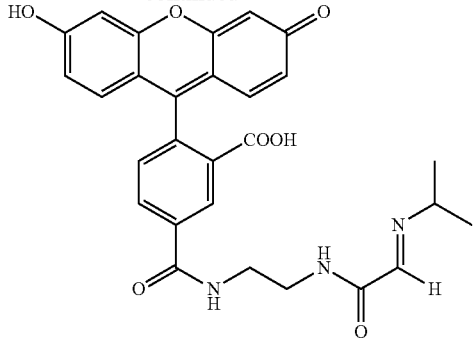

Pro4-de novo-imine

An experiment was performed to determine conversion of an intermediate product, Pro4-de novo-CHO, to a converted product, an imine, with a converting agent, isopropylamine. To a solution of Pro4-de novo-CHO (50 mg, 0.105 mmmol) in DMF (2 mL) was added isopropylamine (20 μL, 0.24 mmol). The resulting solution was stirred at room temperature for 2 days. TLC showed no change in the retention factor (R$_f$; ratio of the migration distance of a substance to the migration distance of the solvent front), but the mass spectrum indicated formation of the desired product. The solvent was reduced under reduced pressure to give Pro4-de novo-imine, the converted product, an imine. The $^1$H nuclear magnetic resonance (NMR) spectrum (300 MHz, dimethylsulfoxide-d$_6$) was consistent with the assigned structure.

Example 7

Conversion of an Intermediate Product, Pro4-de Novo-CHO, to a Converted Product, an Acid with the Converting Agent m-CPBA

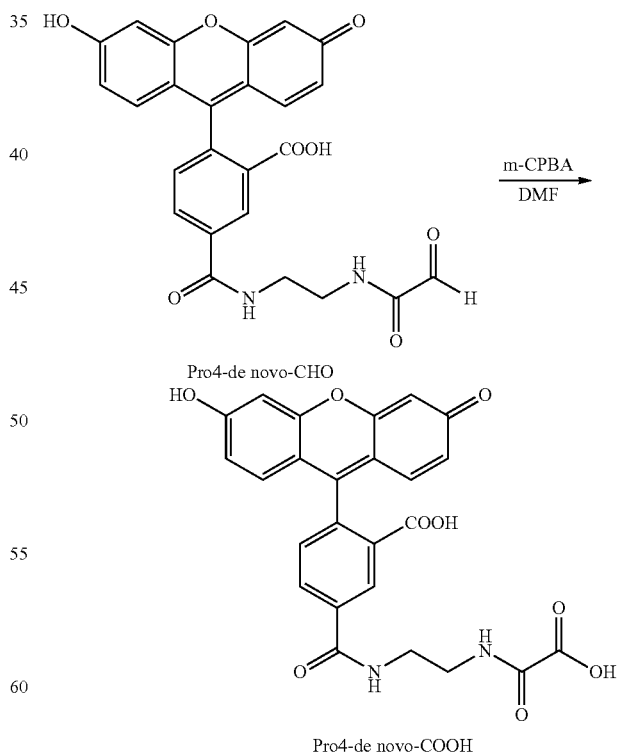

An experiment was performed to determine the conversion of an intermediate product, Pro4-de novo-CHO, to a converted product with m-CPBA as a converting agent. To a solution of Pro4-de novo-CHO (18 mg, 0.038 mmol) in DMF (1 mL) was added m-chloroperbenzoic acid (m-CPBA) (31 mg, 0.138 mmol). The resulting solution was stirred at room temperature for approximately 2 hours. TLC (40:9:1 CH$_2$Cl$_2$—CH$_3$OH-water) revealed completion of the reaction. The mass spectrum was in agreement with the assigned structure.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

The invention claimed is:

1. A method for detecting an analyte in a sample, the method comprising:
    binding a binding compound to an analyte, the binding compound being linked to a releasable tag via a linker, thereby generating a tag-bound analyte complex, wherein the linker contains a singlet oxygen-reactive group, and the releasable tag contains a detection moiety;
    reacting the tag-bound analyte complex with singlet oxygen, thereby cleaving the tag-bound analyte complex at the singlet oxygen-reactive group and generating an intermediate product, the intermediate product containing the detection moiety;
    reacting the intermediate product with a converting agent, thereby generating a converted product, the converted product containing the detection moiety; and
    detecting the presence of the converted product by detecting presence of the detection moiety,
    wherein the detection moiety is detected by generating an electrochemical, fluorescent, or chromogenic signal.

2. The method of claim 1, wherein the linker contains a thioether group.

3. The method of claim 2, wherein the linker has the following structure:

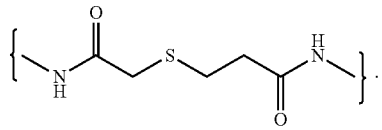

4. The method of claim 1, further comprising subjecting the converted product to electrophoresis.

5. The method of claim 4, wherein the electrophoresis is capillary electrophoresis.

6. The method of claim 1, wherein the detection moiety is a fluorescent label.

7. The method of claim 1, wherein the binding compound contains an antibody, a protein, an aptamer, a nucleic acid, a peptide nucleic acid or a locked nucleic acid.

8. The method of claim 7, wherein the binding compound contains an antibody.

9. The method of claim 1, wherein the converting agent is a reducing agent, an oxidizing agent, a Grignard reagent, hydrogen cyanide, an alcohol, an amine thiol, or a bisulfite.

10. The method of claim 9, wherein the converting agent is a reducing agent.

11. The method of claim 10, wherein the reducing agent is sodium borohydride.

12. The method of claim 9, wherein the converting agent is an oxidizing agent.

13. The method of claim 12, wherein the oxidizing agent is NaOCl/H$_2$O$_2$, H$_2$O$_2$/air, meta-chloroperoxybenzoic acid or a monopersulfate compound.

14. The method of claim 13, wherein the oxidizing agent is meta-chloroperoxybenzoic acid.

15. The method of claim 1, wherein the converted product is an alcohol, an acid, an acetal, an imine, a cyanohydrin, an amine, a thioacetal or a sodium salt of an organic sulfite.

16. The method of claim 15, wherein the converted product is an alcohol.

17. The method of claim 15, wherein the converted product is an acid.

18. The method of claim 1, wherein the analyte is a protein.

19. The method of claim 1, wherein the analyte is a protein complex.

20. The method of claim 18, wherein the analyte is a protein whose expression is related to the prognosis or diagnosis of a disease.

21. The method of claim 20, wherein the disease is a cancer.

22. The method of claim 18, wherein the analyte is a chemokine, a chemokine receptor, a cytokine, or a cytokine receptor.

23. The method of claim 18, wherein the protein is associated with a cell membrane.

24. The method of claim 23, wherein the protein is an enzyme-associated receptor or a G-protein coupled receptor.

25. The method of claim 18, wherein the binding compound includes an antibody.

26. The method of claim 25, wherein the linker contains a thioether group.

27. The method of claim 26, wherein the detection moiety is a fluorescent label, a dye, a chromogenic label, or an electrochemical label.

28. The method of claim 27, wherein the detection moiety is a fluorescent label.

29. The method of claim 28, where the fluorescent label is fluorescein.

30. The method of claim 28, further comprising subjecting the converted product to capillary electrophoresis.

31. The method of claim 30, wherein the releasable tag contains a mobility modifier.

32. The method of claim 31, wherein the intermediate product contains an aldehyde group.

33. The method of claim 32, wherein the converted product contains an alcohol group.

* * * * *

UNITED STATES PATENT AND TRADEMARK OFFICE
CERTIFICATE OF CORRECTION

PATENT NO. : 8,357,277 B2
APPLICATION NO. : 12/744749
DATED : January 22, 2013
INVENTOR(S) : Youssouf Badal et al.

It is certified that error appears in the above-identified patent and that said Letters Patent is hereby corrected as shown below:

In the Specification

Column 1, Line 9, Please delete "parent", please insert -- patent --.

Column 13, Line 17, Please delete "thiother", please insert -- thioether --.

Column 19, Line 17 & 18, Please delete "20 µM A160, 20 µM A315, 5 µM", please insert -- 20 pM A160, 20 pM A315, 5 pM --.

Signed and Sealed this
Eleventh Day of February, 2014

Michelle K. Lee
*Deputy Director of the United States Patent and Trademark Office*